United States Patent
Diaz et al.

[11] Patent Number: 5,905,088
[45] Date of Patent: May 18, 1999

[54] HETEROCYCLIC BIARYL COMPOUNDS AND PHARMACEUTICAL/COSMETIC COMPOSITIONS COMPRISED THEREOF

[75] Inventors: Philippe Diaz, Nice; Etienne Thoreau, Vence, both of France

[73] Assignee: Centre International De Recherches Dermatologiques Galderma, Valbonne, France

[21] Appl. No.: 08/886,039

[22] Filed: Jun. 30, 1997

[30] Foreign Application Priority Data

Jun. 28, 1996 [FR] France .................................. 96 08115

[51] Int. Cl.⁶ .......................... C07D 307/92; A61K 31/34
[52] U.S. Cl. .......................... 514/468; 514/444; 514/844; 514/852; 536/29.1; 548/201; 548/311.4; 548/427; 548/525; 546/284.1; 549/43; 549/60
[58] Field of Search ................ 549/458, 60, 43; 548/427, 201, 311.4, 525; 536/29.1; 546/284.1; 514/444, 468, 844, 852

[56] References Cited

FOREIGN PATENT DOCUMENTS

| 0070531 | 1/1983 | European Pat. Off. . |
| 0292348 | 11/1988 | European Pat. Off. . |
| 2164648 | 3/1986 | United Kingdom . |

OTHER PUBLICATIONS

Chemical Abstracts, vol. 118, No. 15, 1993, Columbus, Ohio, Abstract No. 147416, Jiang et al.

*Primary Examiner*—Bernard Dentz
*Attorney, Agent, or Firm*—Burns, Doane, Swecker & Mathis, L.L.P.

[57] ABSTRACT

Novel pharmaceutically/cosmetically-active heterocyclic biaryl compounds have the structural formula (I):

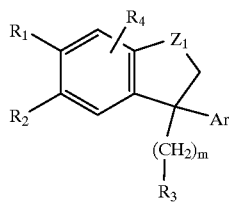

(I)

wherein Ar is a radical having one of the formulae (a)–(h):

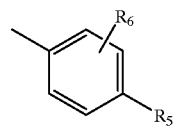

(a)

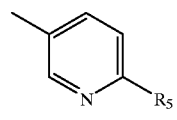

(b)

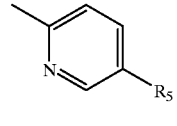

(c)

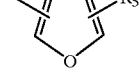

(d)

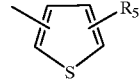

(e)

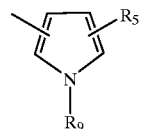

(f)

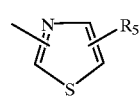

(g)

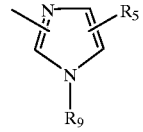

(h)

and are useful for the treatment of a wide variety of disease states, whether human or veterinary, for example dermatological, rheumatic, respiratory, cardiovascular and ophthalmological disorders, as well as for cosmetic applications and for the treatment of mammalian skin and hair conditions/disorders.

55 Claims, 1 Drawing Sheet

X: halogen
$Z_1$: heteroatom

HETEROCYCLIC BIARYL COMPOUNDS AND PHARMACEUTICAL/COSMETIC COMPOSITIONS COMPRISED THEREOF

BACKGROUND OF THE INVENTION

Technical Field of the Invention

The present invention relates to novel aromatic heterocyclic biaryl compounds, and to pharmaceutical/cosmetic compositions comprised thereof; the subject compounds are especially useful in human or veterinary medicine and in cosmetics.

SUMMARY OF THE INVENTION

The compounds of the present invention exhibit activity in the fields of cell differentiation and proliferation. Consequently, these compounds are useful in the topical and systemic treatment of dermatological conditions associated with a keratinization disorder, of dermatological (or other) conditions including an inflammatory, viral and/or immunoallergic component, and of dermal or epidermal proliferations, whether benign or malignant. The subject compounds may be used, in addition, for the treatment of connective tissue degeneration diseases, to combat skin aging, whether photoinduced or chronologic, and to treat cicatrization disorders. They also find application in the ophthalmological field, especially for the treatment of corneopathies.

The compounds according to this invention can also be formulated into cosmetic compositions for body and hair care.

Briefly, the heterocyclic biaryl compounds according to this invention have the following structural formula (I):

(I)

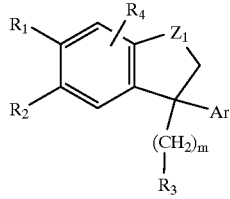

in which $Z_1$ is O, S or N—r'; $R_1$ and $R_2$, taken together, form with the adjacent aromatic ring a 5- or 6- membered ring optionally substituted with one or more methyl groups and/or optionally interrupted by an SO radical, an $SO_2$ radical, or an oxygen or sulfur atom; $R_3$ is (i) a hydrogen atom, a lower alkyl radical, a lower alkenyl radical, a lower alkynyl radical, a halogen atom, a cyano radical or an —O—$R_7$ radical, wherein $R_7$ is as defined below, (ii) a radical

wherein $R_8$ is as defined below, (iii) a radical

wherein r and r' are as defined below; $R_4$ is (i) a hydrogen atom, (ii) a lower alkyl radical, (iii) a halogen atom, (iv) an —$OR_7$ radical, wherein $R_7$ is as defined below, or (v) a lower acyl radical; Ar is a radical selected from among those of the following formulae (a)–(h):

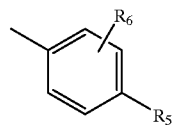
(a)

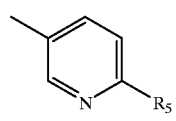
(b)

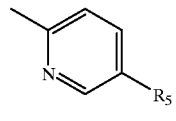
(c)

(d)

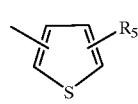
(e)

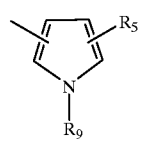
(f)

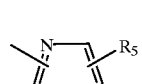
(g)

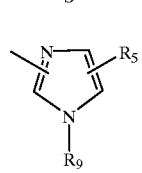
(h)

in which $R_5$ is (i) the radical —$CH_3$, (ii) the radical —$(CH_2)_p$—O—$R_7$, (iii) a radical

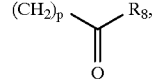

(iv) a radical

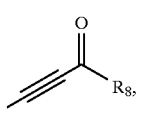

or (v) a radical

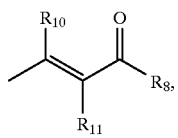

wherein $R_7$, $R_8$, $R_9$, $R_{10}$, $R_{11}$ and p are as defined below; $R_6$ is a hydrogen atom, a halogen atom, a lower alkyl radical, a lower acyl radical or the radical —$OR_7$, wherein $R_7$ is as defined below; the radicals $R_7$, which may be identical or different, are each a hydrogen atom, a lower alkyl radical, an aryl radical, an aralkyl radical, a polyhydroxyalkyl radical, a polyether radical, or a lower acyl radical; the radicals $R_8$, which may be identical or different, are each (a) a hydrogen atom, or a lower alkyl radical, (b) a radical

wherein r and r' are as defined below, or (c) a radical —$OR_{12}$, wherein $R_{12}$ is as defined below; $R_9$ is a hydrogen atom, a lower alkyl radical or a lower acyl radical; the radicals $R_{10}$ and $R_{11}$, which may be identical or different, are each a hydrogen atom or a lower alkyl radical; $R_{12}$ is a hydrogen atom, a lower alkyl radical, a mono- or polyhydroxyalkyl radical, an aryl or aralkyl radical which is (are) optionally substituted, or a sugar or amino acid residue; the radicals r and r', which may be identical or different, are each a protective group comprising an amine function, a hydrogen atom, a lower alkyl radical, an amino acid or sugar residue or, taken together, a heterocycle; m is 0 or 1; and the radicals p, which may be identical or different, are each the numbers 0, 1, 2 or 3; and the salts, racemates, pure optical isomers or mixtures thereof in any proportions.

When the compounds according to the invention exist in the form of pharmaceutically or cosmetically acceptable salts obtained by addition of a base, they are preferably salts of an alkali or alkaline earth metal, of zinc, or of an organic amine.

When the compounds exist in the form of salts, by addition of an acid, they are especially pharmaceutically or cosmetically acceptable salts obtained by addition of an inorganic or organic acid, in particular hydrochloric, sulfuric, acetic, citric, fumaric, hemisuccinic, maleic and mandelic acid.

BRIEF DESCRIPTION OF THE DRAWING

The Figure of Drawing is a reaction scheme for the synthesis of the heterocyclic biaryl compounds according to the present invention.

DETAILED DESCRIPTION OF BEST MODE AND SPECIFIC/PREFERRED EMBODIMENTS OF THE INVENTION

Figure 1:
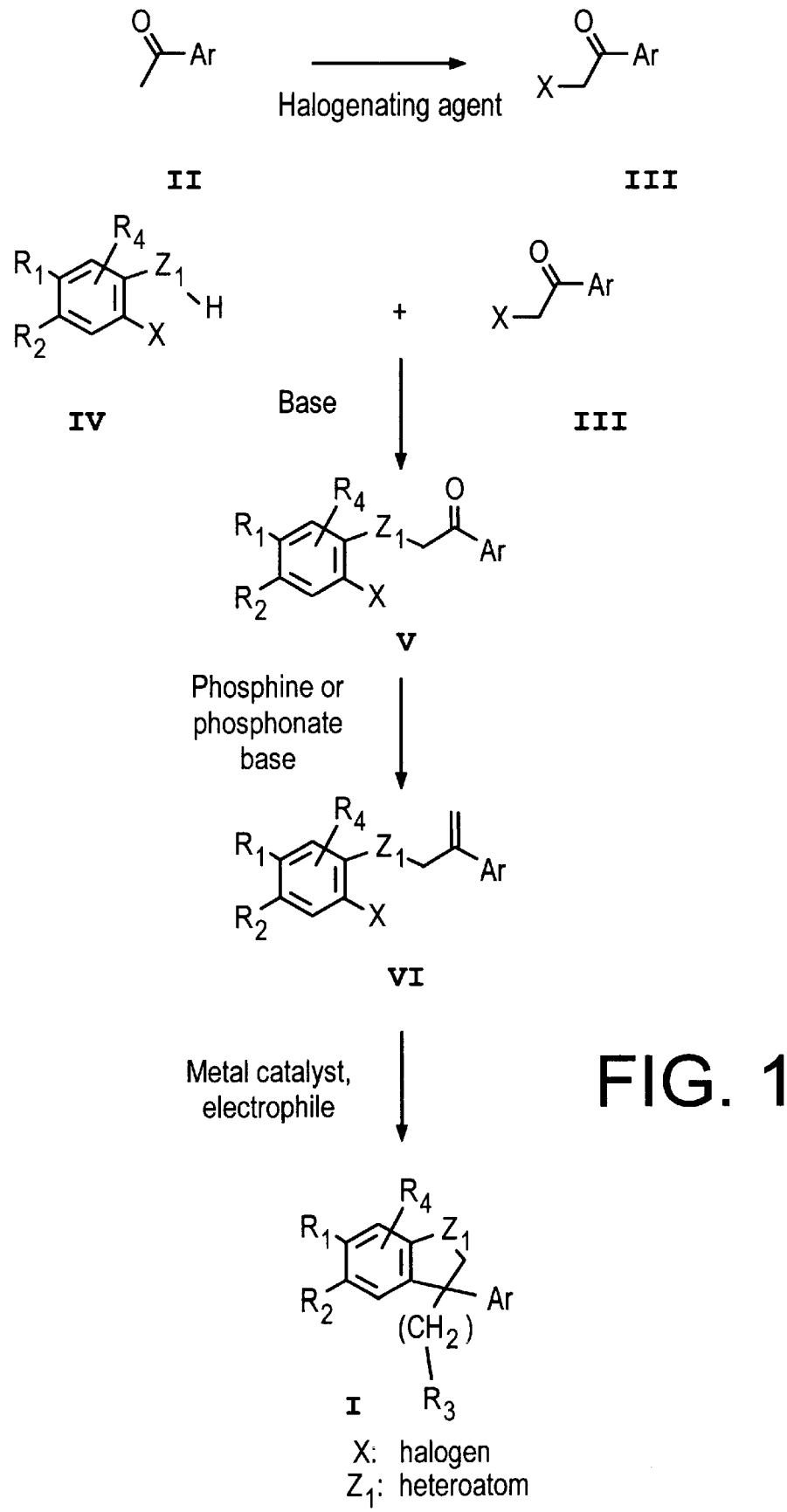

More particularly according to the present invention, by "lower alkyl radical" is intended an alkyl radical having from 1 to 6 carbon atoms, which is linear or branched, optionally substituted with one or more halogen atoms, and preferably methyl, ethyl isopropyl, butyl, tert-butyl and hexyl radicals.

By "lower alkenyl radical" is intended an alkenyl radical having from 1 to 6 carbon atoms, which is linear or branched, comprising one or more ethylenic double bonds, and preferably allyl or vinyl radicals.

By "lower alkynyl radical" is intended an alkynyl radical having from 1 to 6 carbon atoms, which is linear or branched, comprising one or more acetylenic triple bonds.

By "lower acyl radical" is intended an acyl radical having from 1 to 6 carbon atoms, and preferably acetyl, propionyl and pivaloyl radicals.

By "protective group comprising an amine function" are intended the corresponding groups described in *Protecting Groups in Organic Synthesis* by T. W. Greene, Ed. by John Wiley and Sons (1981).

By "cycloalkyl radical" is intended a cyclic or polycyclic alkane radical having from 1 to 10 carbon atoms, optionally substituted with one or more halogen atoms or one or more hydroxyl radicals, and preferably adamantyl or 1-methylcyclohexyl radicals.

By "polyether radical" is intended a radical having from 1 to 6 carbon atoms and from 1 to 3 oxygen or sulfur atoms, such as the methoxymethyl ether, methoxyethoxymethyl ether or methylthio methyl ether radicals.

By "polyhydroxyalkyl radical" is intended a radical having from 1 to 6 carbon atoms and from 1 to 5 hydroxyl groups such as the 2,3-dihydroxypropyl, 2,3,4-trihydroxybutyl, or 2,3,4,5-tetrahydroxypentyl radicals, or the pentaerythritol residue.

By "optionally substituted aryl radical" is intended a phenyl radical optionally substituted with one or more halogen atoms, or one or more hydroxyl or nitro groups, methoxy radicals, or optionally substituted amine functions.

By "optionally substituted aralkyl radical" is intended the benzyl or phenethyl radical optionally substituted with one or more halogen atoms, or one or more hydroxyl or nitro groups, or methoxy radicals.

By "amino acid residue" is intended a residue derived, for example, from one of the 20 amino acids of L or D configuration which are constituents of mammalian proteins.

By "sugar residue" is intended a residue derived, for example, from glucose, galactose, mannose or glucuronic acid.

And by "heterocycle" is preferably intended a piperidino, morpholino, pyrrolidino or piperazino radical, optionally substituted at the 4 position with a $C_1$–$C_6$ alkyl radical or a mono- or polyhydroxyalkyl radical as defined above.

According to the present invention, the compounds of formula (I) which are more particularly preferred are those for which at least one, and preferably all, of the conditions below are satisfied:

$R_3$ is a hydrogen atom,
$R_4$ is a hydrogen atom,
$R_5$ is a radical of formula (iii), (iv) or (v),
$R_6$ is a hydrogen atom,
$R_8$ is an $OR_{12}$ radical,
$R_{12}$ is a hydrogen atom or a lower alkyl radical,
Ar is a radical of formula (a), $Z_1$ is an oxygen atom,
m=1,
p=0.

Among the compounds of formula (I) according to the present invention, particularly representative are the following:

4-(3,5,5,8,8-Pentamethyl-2,3,5,6,7,8-hexahydronaphtho [2,3-b]furan-3-yl)benzoic acid;

(+)-4-(3,5,5,8,8-Pentamethyl-2,3,5,6,7,8-hexahydronaphtho[2,3-b]furan-3-yl)benzoic acid;

4-(3,5,5,8,8-Pentamethyl-2,3,5,6,7,8-hexahydronaphtho [2,3-b]thiophen-3-yl)benzoic acid;

(−)-4-(3,5,5,8,8-Pentamethyl-2,3,5,6,7,8-hexahydronaphtho[2,3-b]furan-3-yl)benzoic acid;

Ethyl 4-(3,5,5,8,8-pentamethyl-2,3,5,6,7,8-hexahydronaphtho[2,3-b]furan-3-yl)benzoate;

Ethyl (+)-4-(3,5,5,8,8-pentamethyl-2,3,5,6,7,8-hexahydronaphtho[2,3-b]furan-3-yl)benzoate;

Ethyl (−)-4-(3,5,5,8,8-pentamethyl-2,3,5,6,7,8-hexahydronaphtho[2,3-b]furan-3-yl)benzoate;

Methyl [5-(3,5,5,8,8-pentamethyl-2,3,5,6,7,8-hexahydronaphtho[2,3-b]furan-3-yl)thiophen-3-yl] carboxylate;

[5-(3,5,5,8,8-Pentamethyl-2,3,5,6,7,8-hexahydronaphtho[2,3-b]furan-3-yl)thiophen-3-yl]carboxylic acid;

[5-(3,5,5,8,8-Pentamethyl-2,3,5,6,7,8-hexahydronaphtho[2,3-b]furan-3-yl)thiophen-2-yl]carboxylic acid;

[5-(3,5,5,8,8-Pentamethyl-2,3,5,6,7,8-hexahydronaphtho[2,3-b]furan-3-yl)thiophen-3-yl] methanol;

[5-(3,5,5,8,8-Pentamethyl-2,3,5,6,7,8-hexahydronaphtho[2,3-b]furan-3-yl)thiophen-3-yl]carbaldehyde;

Ethyl [5-(3,5,5,8,8-pentamethyl-2,3,5,6,7,8-hexahydronaphtho[2,3-b]furan-3-yl)thiophen-3-yl] acrylate;

[5-(3,5,5,8,8-pentamethyl-2,3,5,6,7,8-hexahydronaphtho[2,3-b]furan-3-yl)thiophen-3-yl]acrylic acid;

Methyl [5-(3,5,5,8,8-pentamethyl-2,3,5,6,7,8-hexahydronaphtho[2,3-b]furan-3-yl)thiophen-3-yl] propynoate;

[5-(3,5,5,8,8-pentamethyl-2,3,5,6,7,8-hexahydronaphtho[2,3-b]furan-3-yl)thiophen-3-yl]propynoic acid.

The present invention also features the processes for preparing the compounds of formula (I), in particular according to the reaction schemes illustrated in the Figure of Drawing.

Thus, the compounds of formula (I) may be obtained (Figure of Drawing) from the ketone II by halogenation, for example by means of a brominating agent such as bromine. The resulting compound III is then coupled with the compound IV, in the presence of a base such as potassium carbonate or sodium hydride. The coupled derivative V is subjected to the action of a phosphine or a phosphonate in the presence of a base to give the compound VI. The compound VI is cyclized by the action of a metal catalyst such as palladium diacetate, in the presence of a hydride donor such as formic acid or a nucleophile such as vinyl tributyl tin or lithium acetate and, if necessary, a base. The addition of silver salts or silver-exchanged zeolites, such as $Ag_3PO_4$ and of chiral phosphines such as Binap promote an asymmetric cyclization.

The compounds of formula (I) are also starting materials for the synthesis of other compounds. These other derivatives are obtained via conventional methods of chemical synthesis, such as those described in *Advanced Organic Chemistry* by J. March; John Wiley and Sons, 1985.

For example, functional modifications of the $R_1$ group may be carried out as indicated below:

| | |
|---|---|
| carboxylic acid | → ester |
| ester | → carboxylic acid |
| acid | → acid chloride |
| acid chloride | → amide |
| acid | → amide |
| acid | → alcohol |
| alcohol | → aldehyde |
| amide | → amine |
| thiol | → thioether |
| thioether | → sulfoxide |
| thioether | → sulfone |
| sulfonic acid | → sulfonic ester |
| sulfonic acid | → sulfonamide |
| sulfinic acid | → sulfinic ester |

The present invention also features therapeutic/pharmaceutical applications of the compounds of formula (I).

Certain of the subject compounds exhibit activity in a test which entails identifying molecules which are agonists of the RXRs, as described in French patent application No. 95-07301 filed Jun. 19, 1995 and assigned to the assignee hereof. This test comprises the following steps: (i) a sufficient amount of a compound which is an active ligand of at least one receptor of the super family of the steroid/thyroid receptors, other than a ligand specific for the RXR receptors, and capable of heterodimerization with the RXRs, such as an agonist molecule for the RARs is topically applied over a portion of the skin of a mammal, (ii) a molecule which exhibits an agonist activity for the RXRs is administered via the systemic or topical route over this same portion of the skin of the mammal, before, during or after step (i), and (iii) the response is evaluated on the portion of the skin of the mammal thus treated. Thus, the response to a topical application, on the ear of a mammal, of an agonist molecule for the RARs which corresponds to an increase in the thickness of this ear may be increased by the administration, via the systemic or topical route, of an agonist molecule for the RXRs. Certain of the subject compounds according to the invention also exhibit activity in the test of differentiation of mouse embryonic teratocarcinoma cells (F9) (*Cancer Research*, 43, p. 5268 (1983) and/or in the test of inhibition of ornithine decarboxylase after induction by TPA in mice (*Cancer Research*, 38, p. 793–801 (1978)). These tests demonstrate the activities of the subject compounds, respectively, for cell differentiation and proliferation applications.

The compounds according to the invention are particularly well suited for the treatment of dermatological, rheumatic, respiratory, as well as ophthalmological disorders, in particular in the following fields of therapy.

(1) for treating dermatological conditions associated with a keratinization disorder related to differentiation and proliferation, especially for treating acne vulgaris, comedo-type acne, polymorphic acne, rosacea, nodulocystic acne, acne conglobata, senile acne, secondary acne such as solar acne, acne medicamentosa or occupational acne;

(2) for treating other types of keratinization disorders, especially ichtyoses, ichtyosiform states, Darier's disease, keratosis palmaris and plantaris, leukoplasia and leukoplasiform states, cutaneous or mucosal (buccal) lichen;

(3) for treating other dermatological conditions associated with a keratinization disorder manifesting an inflammatory and/or immunoallergic component, and, especially, all forms of psoriasis, whether cutaneous, mucosal or ungual, and even psoriatic rheumatism, or cutaneous atopy, such as eczema or respiratory atopy or gingival hypertrophy; the subject compounds may also be used for treating certain inflammatory conditions which do not exhibit keratinization disorder;

(4) for treating any dermal or epidermal proliferations, whether benign or malignant, whether of viral origin or not, such as verruca vulgaris, verruca plana and epidermodysplasia verruciformis, oral or florid papillomatoses and proliferations which may be induced by ultraviolet radiation, especially in the case of baso- and spinocellular epithelioma;

(5) for treating other dermatological disorders such as bullous dermatoses and collagen diseases;

(6) for treating certain ophthalmological disorders, especially corneopathies;

(7) For repairing or combating skin aging, whether photoinduced or chronologic, or for reducing pigmentations and actinic keratoses, or any pathologies associated with chronologic or actinic aging;

(8) for preventing or curing the stigmas of epidermal and/or dermal atrophy induced by local or systemic corticosteroids, or any other form of cutaneous atrophy;

(9) for preventing or treating cicatrization disorders or preventing or repairing vibices;

(10) for combating disorders of the sebaceous function, such as hyperseborrhoea of acne or simple seborrhoea;

(11) for the treatment or prevention of cancerous or precancerous states, more particularly promyelocytic leukemias;

(12) for the treatment of inflammatory conditions such as arthritis;

(13) for the treatment of any condition of viral origin at the cutaneous level, such as Kaposis' syndrome, or in general;

(14) for the prevention or treatment of alopecia;

(15) for the treatment of dermatological or general conditions including an immunological component;

(16) for the treatment of conditions of the cardiovascular system, such as arteriosclerosis or hypertension, as well as non-insulin-dependent diabetes;

(17) for the treatment of cutaneous disorders due to exposure to U.V. radiation.

For the aforesaid therapeutic or pharmaceutical applications, the compounds according to the invention may advantageously be used in combination with other compounds displaying a retinoid-type activity, with vitamins D or derivatives thereof, with corticosteroids or estrogens, in association with antioxidants, with α-hydroxy or α-keto acids or derivatives thereof, or alternatively with potassium channel blockers.

By "vitamins D or derivatives thereof" are intended, for example, the derivatives of vitamin $D_2$ or $D_3$ and in particular 1,25-dihydroxyvitamin $D_3$.

By "anti-free radicals" are intended, for example, α-tocopherol, superoxide dismutase, ubiquinol or certain metal-chelating agents.

By "α-hydroxy or α-keto acids or derivatives thereof" are intended, for example, lactic, malic, citric, glycolic, mandelic, tartaric, glyceric or ascorbic acids, or derivatives of salicylic acid, or the salts, amides and esters thereof.

By "potassium channel blockers" are intended, for example, Minoxidil (2,4-diamino-6-piperidinopyrimidine 3-oxide) and derivatives thereof.

The present invention thus also features novel pharmaceutical/cosmetic compositions, especially for the treatment of the aforesaid disease states, which comprise, in a pharmaceutically acceptable carrier, diluent or vehicle, at least one compound of formula I as described above.

The administration of the compounds according to the invention may be carried out via the systemic, enteral, parenteral, topical or ocular route.

For enteral administration, the medicanal/pharmaceutical compositions may be in the form of tablets, gelatin capsules, sugar-coated tablets, syrups, suspensions, solutions, powders, granules, emulsions, lipid or polymeric microspheres or nanospheres or vesicles permitting controlled release. For parenteral administration, the compositions may be in the form of solutions or suspensions for infusion or for injection.

The compounds according to the invention are generally administered at a daily dose of about 0.01 mg/kg to 100 mg/kg body weight, and this in a regimen or rate of 1 to 3 doses per diem.

For topical administration, the pharmaceutical compositions based on compounds according to the invention are more particularly intended for the treatment of the skin and the mucous membranes and are provided in the form of salves, creams, milks, ointments, powders, impregnated pads, solutions, gels, sprays, lotions or suspensions. They may also be provided in the form of lipid or polymeric microspheres or nanospheres or vesicles or polymeric patches and hydrogels permitting controlled release. These compositions for topical administration may be provided either in anhydrous form, or in aqueous form according to the particular clinical indication.

For ocular administration, they are principally collyria.

These pharmaceutical compositions contain at least one compound of formula (I), preferably at a concentration ranging from 0.001% to 5% by weight relative to the total weight of the composition.

The compounds of formula (I) according to the invention also find application in the cosmetic field, in particular for body and hair care and especially for the treatment of skins which tend to have acne, for hair regrowth, against hair loss, for combating the greasy appearance of the skin or the hair, in the protection against the harmful effects of the sun or in the treatment of physiologically dry skins, for preventing and/or combating photoinduced or chronologic aging.

For cosmetic applications, the compounds according to the invention may advantageously be used in combination with other compounds displaying retinoid-type activity, with vitamins D or derivatives thereof, with corticosteroids, in association with anti-free radicals, with α-hydroxy or α-keto acids or derivatives thereof, or with ion channel blockers.

These various active agents used in association with the compounds of the present invention are defined above.

The present invention therefore also features cosmetic compositions containing, in a cosmetically acceptable carrier, diluent or vehicle, at least one compound of formula (I). Such compositions are advantageously in the form of a cream, a milk, a lotion, a gel, lipid or polymeric microspheres or nanospheres or vesicles, a soap or a shampoo.

The concentration of the compound of formula (I) in the cosmetic compositions advantageously ranges from 0.001% to 3% by weight relative to the total weight of the composition.

The medicinal and cosmetic compositions according to the invention may, in addition, contain inert or even pharmacodynamically or cosmetically active additives and adjuvants, or combinations of these additives, and, especially: wetting agents; depigmenting agents such as hydroquinone, azelaic acid, caffeic acid or kojic acid; emollients; moisturizing agents such as glycerol, PEG 400, thiamorpholinone and derivatives thereof or urea; antiseborrheic or antiacne agents, such as S-carboxymethylcysteine, S-benzylcysteamine, salts and derivatives thereof, or benzoyl peroxide; antibiotics such as erythromycin and esters thereof, neomycin, clindamycin and esters thereof, tetracyclines; antifungal agents such as ketoconazole or 4,5-polymethylene-3-isothiazolinones; agents promoting hair regrowth, such as Minoxidil (2,4-diamino-6-piperidinopyrimidine 3-oxide) and derivatives thereof, Diazoxide (7-chloro 3-methyl-1,2,4-benzothiadiazine 1,1-dioxide) and Phenytoin (5,4-diphenyl-2,4-imidazolidinedione); nonsteroidal anti-inflammatory agents; carotenoids and especially β-carotene; anti-psoriatic agents such as anthralin and derivatives thereof and, lastly, 5,8,11,14-eicosatetraynoic and 5,8,11-eicosatrynoic acids, and esters and amides thereof.

The compositions according to the invention may also contain flavor- or taste-enhancing agents, preservatives such as esters of para-hydroxybenzoic acid, stabilizing agents, moisture regulating agents, pH regulating agents, osmotic pressure modifying agents, emulsifying agents, UV-A- and UV-B- screening agents, antioxidants, such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

A. EXAMPLES OF COMPOUNDS SYNTHESIZED VIA THE REACTION SCHEME SHOWN IN THE FIGURE OF DRAWING

Example 1

Synthesis of ethyl 4-(3,5,5,8,8-pentamethyl-2,3,5,6,7,8-hexahydronaphtho[2,3-b]furan-3yl)benzoate (a) Preparation of 3-iodo-5,5,8,8-tetramethyl-5,6,7,8-tetrahydronaphthalen-2-ol A 3.6% sodium perchlorate solution was added dropwise to a mixture of 5,5,8,8-tetramethyl-5,6,7,8tetrahydronaphthalen-2-ol(6.35 g, 31.1 mmol), sodium hydroxide (1.23 g, 34.2 mmol) and sodium iodide (4.6 g, 31.1 mmol) in methanol (115 ml), at 0° C. The mixture was maintained under stirring for two hours at 0° C. 33 ml of a 10% sodium thiosulfate solution were added. After stirring, the mixture was acidified with hydrochloric acid to pH 1. It was extracted with 200 ml of ethyl ether. The organic phase was washed twice with 400 ml of water, dried over magnesium sulfate and concentrated in a rotary evaporator under vacuum at 40° C.

The desired compound was recrystallized from heptane.
Analysis:
White solid. Mass: 5.67 g. Yield: 55%. m.p.=103° C. $^1$H NMR (CDCl$_3$, 250 MHz); 1.23 (6H, s), 1.24 (6H, s), 1.64 (4H, s), 5.04 (1H, s), 6.93 (1H Ar, s), 7.59 (1H Ar, s).
$^{13}$C NMR (CDCl$_3$, 250 MHz): 31.49, 31.75, 33.53, 34.19, 34.63, 34.76, 82.86, 112.47, 135.93, 139.73, 147.67, 152.16.

(b) Preparation of ethyl 4-bromoactetyl benzoate

A solution of bromine (1.6 ml) in 15 ml of CH$_2$Cl$_2$ wax added dropwise to a solution of ethyl 4-acetyl benzoate (5.28 g, 27 mmol), of dioxane (30 ml) and ethyl ether (30 ml). The stirring was continued for 1 h and then the mixture was poured into 100 g of ice and extracted with 100 ml of ethyl ether. The organic phase was washed twice with 100 ml of water, dried over magnesium sulfate and concentrated in a rotary evaporator under vacuum.

The desired compound was purified by recrystallization from heptane.

Analysis:
White solid. Mass: 5.03 g. Yield: 69%. m.p.=71° C. $^1$H NMR (CDCl$_3$, 250 MHz): 1.42 (3H, t, J=7.5 Hz), 4.42 (2H, 9, J=7.5 Hz), 4.48 (2H, s), 8.04 (2H Ar, d, J=8.75 Hz), 8.16 (2H Ar, d, J=8.75 Hz).
$^{13}$C NMR (CDCl$_3$, 250 MHz): 14.18, 30.64, 61.50, 128.74, 129.87, 134.90, 136.97, 165.37, 190.76.

(c) Preparation of ethyl 4-[(3-iodo-5,5,8,8-tetramethyl-5,6,7,8-tetrahydro-naphthalen-2-yloxy)-acetyl]benzoate A solution of 3-iodo-5,5,8,8-tetramethyl-5,6,7,8-tetrahydronaphthalen-2-ol (5.6 g, 17 mmol), ethyl 4-bromoacetyl benzoate (4.6 g, 17 mmol), and potassium carbonate (2.4 g, 17.4 mmol) in methyl ethyl ketone (150 ml), was heated under reflux for 8 h. The reaction medium was filtered and then concentrated in a rotary evaporator. 200 ml of water and 200 ml of ethyl ether was added. After stirring and decantation, the organic phase was washed twice with 200 ml of water, dried over magnesium sulfate and concentrated in a rotary evaporator under vacuum at 40° C.

The desired compound was purified by flash chromatography on a silica column (80% CH$_2$Cl$_2$, 20% heptane).
Analysis:
White solid. Mass: 4.7 g. Yield: 53%. m.p.=137° C. $^1$H NMR (CDCl$_3$, 250 MHz): 1.20 (6H, s), 1.22 (6H, s), 1.42 (3H, t, J=7.5 Hz), 1.63 (4H, s), 4.41 (2H, q, J=7.5 Hz), 5.21 (2H, s), 6.68 (1H Ar, s), 7.64 (1H Ar, S), 8.11 (2H Ar, d, J=8.75 Hz), 8.14 (2H Ar, d, J=8.75 Hz).
$^{13}$C NMR (CDCl$_3$, 250 MHz): 14.05, 31.41, 31.53, 33.53, 34.55, 34.60, 61.30, 72.58, 83.27, 110.75, 128.41, 129.60, 134.62, 137.44, 137.65, 140.88, 146.68, 154.12, 165.40, 194.86.

(d) Preparation of ethyl 4-[(3-iodo-5,5,8,8-tetramethyl-5,6,7,8-tetrahydro-naphthalen-2-yloxy)-1-propenyl]benzoate A 30% sodium methoxide solution (1.31 ml) was added over 8 hours to a mixture of ethyl 4-[(3-iodo-5,5,8,8-tetramethyl-5,6,7,8-tetrahydronaphthalen-2 -yloxy)-acetyl]benzoate (3.6 g, 7 mmol) and methyltriphenylphosphine bromide (3.4 g, 9.5 mmol) in THF (40 ml).

The mixture was stirred for 36 h at room temperature. The mixture was concentrated in a rotary evaporator under vacuum at 40° C. It was extracted with 90 ml of ethyl ether and 90 ml of water. After decantation, the organic phase was washed twice with 90 ml of water, dried over anhydrous magnesium sulfate and concentrated in a rotary evaporator under vacuum at 40° C.

The desired compound was purified by flash chromatography on a silica column (60% CH$_2$Cl$_2$, 40% heptane).
Analysis:
White solid. Mass: 2.79 g. Yield: 77%. m.p.=88° C. $^1$H NMR (CDCl$_3$, 250 MHz): 1.24 (6H, s), 1.25 (6H, s), 1.40 (3H, t, J=7.5 Hz), 1.65 (4H, s), 4.39 (2H, q, J=7.5 Hz), 4.91 (2H, s), 5.71 (2H, s), 6.76 (1H Ar, s), 7.57 (2H Ar, d, J=8.75 Hz), 7.65 (1H Ar, s), 8.04 (2H Ar, d, J=8.75 Hz).
$^{13}$C NMR (CDCl$_3$, 250 MHz): 14.33, 31.71, 31.80, 33.72, 34.56, 34.90, 60.95, 70.60, 83.93, 110.70, 116.98, 126.18, 126.24, 129.71, 129.75, 129.88, 137.58, 140.25, 142.26, 142.77, 146.61, 154.70, 166.33.

(e) Synthesis of ethyl 4-(3,5,5,8,8-pentamethyl-2,3,5,6,7,8-hexahydronaphtho[2,3-b]furan-3-yl) benzoate A mixture of tributylamine (0.55 ml, 3.8 mmol), palladium diacetate (22 mg, 0.1 mmol), formic acid (0.042 ml, 1.1 mmol) and ethyl 4-[(3-iodo-5,5,8,8-tetramethyl-5,6,7,8-tetrahydro naphthalen-2-yloxy)-1-propenyl]benzoate (520 mg, 1 mmol) in acetonitrile (15 ml), was heated at 60° C. for 4 h. The reaction medium was concentrated in a rotary evaporator under vacuum at 40° C. 20 ml of water and 20 ml of ethyl ether were added. After decantation, the organic phase was washed twice with 20 ml of water, dried over magnesium sulfate and concentrated in a rotary evaporator under vacuum at 40° C.

The desired compound was purified by flash chromatography on a silica column (80% $CH_2Cl_2$, 20% heptane).
Analysis:

White solid. Mass: 315 mg. Yield: 80%. m.p.=139° C. $^1$H NMR ($CDCl_3$, 250 MHz): 1.18 (3H, s), 1.22 (3H, s), 1.28 (6H, s), 1.38 (3H, t, J=7.5 Hz), 1.66 (4H, s), 1.75 (3H, s), 4.36 (2H, q, J=7.5 Hz), 4.42 (2H, d, J=8.75 Hz), 4.52 (2H, d, J=8.75 Hz), 6.81 (1H Ar, s), 6.94 (1H Ar, s), 7.36 (2H Ar, d, J=8.75 Hz), 7.98 (2H Ar, d, J=8.75 Hz).

$^{13}$C NMR ($CDCl_3$, 250 MHz): 14.34, 26.07, 32.01, 32.09, 32.28, 34.15, 34.72, 35.14, 35.24, 50.27, 60.87, 85.69, 107.07, 121.74, 126.48, 128.69, 129.66, 132.20 137.78, 145.61, 151.84, 157.63, 166.43.

Example 2

Synthesis of 4-(3,5,5,8,8-pentamethyl-2,3,5,6,7,8-hexahydronaphtho[2,3-b]furan-3-yl)benzoic acid A mixture of ethyl 4-(3,5,5,8,8-pentamethyl-2,3,5,6,7,8-hexahydronaphtho[2,3-b]furan-3-yl)benzoate (200 mg, 0.5 mmol), sodium hydroxide (100 mg, 2.4 mmol) and lithium hydroxide (100 mg, 2.4 mmol) in 5 ml of a solution of THF, methanol and water (5/1/1) was heated under reflux for 24 h. The reaction medium was concentrated in a rotary evaporator under vacuum at 40° C. After adding 5 ml of water and 5 ml of ethyl ether and acidifying with a concentrated hydrochloric acid solution to pH 1, the organic phase was washed twice with 5 ml of water, dried over magnesium sulfate and concentrated in a rotary evaporator under vacuum at 40° C. The solids obtained were washed with heptane.
Analysis:

White Solid. Mass: 152 mg. Yield: 82%. m.p.=245° C. $^1$H NMR (DMSO, 250 MHz): 1.19 (3H, s), 1.23 (3H, s), 1.29 (6H, s), 1.66 (4H, s), 1.77 (3H, s), 4.44 (2H, q, J=8.5 Hz), 4.54 (2H, d, J=8.5 Hz), 6.82 (1H Ar, s), 6.95 (1H Ar, s), 7.40 (2H Ar, d, J=8.75 Hz), 8.05 (2H Ar, d, J=8.75 Hz).

$^{13}$C NMR (DMSO, 250 MHz): 26.43, 32.43, 32.51, 32.70, 34.58, 35.15, 35.54, 35.64, 50.77, 86.06, 107.55, 122.16, 127.08, 127.85, 130.78, 132.48, 138.28, 146.13, 153.45, 158.04, 172.23.

Example 3

Synthesis of ethyl (+)-4-(3,5,5,8,8-pentamethyl-2,3,5,6,7,8-hexahydronaphtho[2,3-b]furan-3-yl)benzoate A mixture of calcium carbonate (200 mg, 2 mmol), palladium diacetate (22 mg, 0.1 mmol), sodium formate (136 mg, 2 mmol) and ethyl 4-[(3-iodo-5,5,8,8-tetramethyl-5,6,7,8-tetrahydronaphthalen-2-yloxy)-1-propenyl]benzoate (520 mg 1 mmol), (S)-(−)-2,2'-bis(diphenylphosphino)-1,1'-binaphthyl and silver-exchanged zeolite (Aldrich 36,660-9) in acetonitrile (15 ml), was heated at 60° C. for 4 d. The reaction medium was filtered on celite, concentrated in a rotary evaporator under vacuum at 40° C. 20 ml of water and 20 ml of ethyl ether were added. After decantation, the organic phase was washed twice with 20 ml of water, dried over magnesium sulfate and concentrated in a rotary evaporator under vacuum at 40° C.

The desired compound was purified by flash chromatography on a silica column (80% $CH_2Cl_2$, 20% heptane).
Analysis:

White solid. Mass: 105 mg. Yield: 27%. m.p.=139° C., $\alpha_d$[$CHCl_3$]: +122.4.1 $^1$H NMR ($CDCl_3$, 250 MHz): 1.18 (3H, s), 1.22 (3H, s), 1.28 (6H, s), 1.38 (3H, t, J=7.5 Hz), 1.66 (4H, s), 1.75 (3H, s), 4.36 (2H, q, J=7.5 Hz), 4.42 (2H, d, J=8.75 Hz), 4.52 (2H, d J=8.75 Hz), 6.81 (1H Ar, s), 6.94 (1H Ar, s), 7.36 (2H Ar, d, J=8.75 Hz), 7.98 (2H Ar, d, J=8.75 Hz).

$^{13}$C NMR ($CDCl_3$, 250 MHz): 14.34, 26.07, 32.01, 32.09, 32.28, 34.15, 34.72, 35.14, 35.24, 50.27, 60.87, 85.69, 107.07, 121.74, 126.48, 128.69, 129.66, 132.20 137.78, 145.61, 151.84, 157.63, 166.43.

Example 4

Synthesis of (+)-4-(3,5,5,8,8-Pentamethyl-2,3,5,6,7,8-hexahydronaphtho[2,3-b]furan-3-yl)benzoic acid A mixture of ethyl (+)-4-(3,5,5,8,8-pentamethyl-2,3,5,6,7,8-hexahydronaphtho[2,3-b]furan3-yl)benzoate (200 mg, 0.5 mmol), sodium hydroxide (100 mg, 2.4 mmol) and lithium hydroxide (100 mg, 2.4 mmol), in 5 ml of a solution of THF, methanol and water (5/1/1) was heated under reflux for 24 h. The reaction medium was concentrated in a rotary evaporator under vacuum at 40° C. After adding 5 ml of water and 5 ml of ethyl ether and acidifying with a concentrated hydrochloric acid solution to pH 1, the organic phase was washed twice with 5 ml of water, dried over magnesium sulfate and concentrated in a rotary evaporator under vacuum at 40° C. The solids obtained were washed with heptane.
Analysis:

White solid. Mass: 152 mg. Yield: 82%. m.p.=245° C. $^1$H NMR (DMSO, 250 MHz): 1.19 (3H, s), 1.23 (3H, s), 1.29 (6H, s), 1.66 (4H, s), 1.77 (3H, s), 4.44 (2H, q, J=8.5 Hz), 4.54 (2H, d, J=8.5 Hz), 6.82 (1H Ar, s), 6.95 (1H Ar, s), 7.40 (2H Ar, d, J=8.75 Hz), 8.05 (2H Ar, d, J=8.75 Hz).

$^{13}$C NMR (DMSO, 250 MHz): 26.43, 32.43, 32.51, 32.70, 34.58, 35.15, 35.54, 35.64, 50.77, 86.06, 107.55, 122.16, 127.08, 127.85, 130.78, 132.48, 138.28, 146.13, 153.45, 158.04, 172.23.

Example 5

Synthesis of ethyl (−)-4-(3,5,5,8,8-pentamethyl-2,3,5,6,7,8-hexahydronaphtho[2,3-b]furan-3-yl)benzoate A mixture of calcium carbonate (200 mg, 2 mmol), palladium diacetate (22 mg, 0.1 mmol), sodium formate (136 mg, 2 mmol) and ethyl 4-[(3-iodo-5,5,8,8-tetramethyl-5,6,7,8-tetrahydronaphthalen-2-yloxy)-1-propenyl]benzoate (520 mg, 1 mmol), (R)-(+)-2,2'-bis(diphenylphosphino)-1,1'-binaphthyl and silver-exchanged zeolite (Aldrich 36,660-9) in acetonitrile (15 ml), was heated at 60° C. for 4 days. The reaction medium was filtered on celite, concentrated in a rotary evaporator under vacuum at 40° C. 20 ml of water and 20 ml of ethyl ether were added. After decantation, the organic phase was washed twice with 20 ml of water, dried over magnesium sulfate and concentrated in a rotary evaporator under vacuum at 40° C.

The desired compound was purified by flash chromatography on a silica column (80% $CH_2Cl_2$, 20% heptane).
Analysis:

White solid. Mass: 85 mg. Yield: 22%. m.p.=139° C., $\alpha_d$[$CHCl_3$]: −110.2. $^1$H NMR ($CDCl_3$, 250 MHz): 1.18 (3H, s), 1.22 (3H, s), 1.28 (6H, s), 1.38 (3H, t, J=7.5 Hz), 1.66 (4H, s), 1.75 (3H, s), 4.36 (2H, q, J=7.5 Hz), 4.42 (2H, d, J=8.75 Hz), 4.52 (2H, d J=8.75 Hz), 6.81 (1H Ar, s), 6.94 (1H Ar, s), 7.36 (2H Ar, d, J=8.75 Hz), 7.98 (2H Ar, d, J=8.75 Hz).

$^{13}$C NMR (CDCl$_3$, 250 MHz): 14.34, 26.07, 32.01, 32.09, 32.28, 34.15, 34.72, 35.14, 35.24, 50.27, 60.87, 85.69, 107.07, 121.74, 126.48, 128.69, 129.66, 132.20 137.78, 145.61, 151.84, 157.63, 166.43.

Example 6

Synthesis of (–)-4-(3,5,5,8,8-pentamethyl-2,3,5,6,7, 8-hexahydronaphtho[2.3-b]furan-3-yl)benzoic acid A mixture of ethyl (–)-4-(3,5,5,8,8-pentamethyl-2,3,5,6, 7,8-hexahydronaphtho[2,3-b]furan-3-yl)benzoate (200 mg, 0.5 mmol), sodium hydroxide (100 mg, 2.4 mmol), and lithium hydroxide (100 mg, 2.4 mmol) in 5 ml of a solution of THF, methanol and water (5/1/1) was heated under reflux for 24 h. The reaction medium was concentrated in a rotary evaporator under vacuum at 40° C. After adding 5 ml of water and 5 ml of ethyl ether and acidifying with a concentrated hydrochloric acid solution to pH 1, the organic phase was washed twice with 5 ml of water, dried over magnesium sulfate and concentrated in a rotary evaporator under vacuum at 40° C. The solid obtained was washed with heptane.
Analysis:
White solid. Mass: 152 mg. Yield: 82%. m.p.=245° C.
$^1$H NMR (DMSO, 250 MHz): 1.19 (3H, s), 1.23 (3H, s), 1.29 (6H, s), 1.66 (4H, s), 1.77 (3H, s), 4.44 (2H, q, J=8.5 Hz), 4.54 (2H, d, J=8.5 Hz), 6.82 (1H Ar, s), 6.95 (1H Ar, s), 7.40 (2H Ar, d, J=8.75 Hz), 8.05 (2H Ar, d, J=8.75 Hz).
$^{13}$C NMR (DMSO, 250 MHz): 26.43, 32.43, 32.51, 32.70, 34.58, 35.15, 35.54, 35.64, 50.77, 86.06, 107.55, 122.16, 127.08, 127.85, 130.78, 132.48, 138.28, 146.13, 153.45, 158.04, 172.23.

Example 7

Synthesis of methyl [5-(3,5,5,8,8-pentamethyl-2,3,5, 6,7,8-hexahydronaphtho[2,3-b]furan-3-yl) thiophen-3-yl]carboxylate (a) Preparation of methyl 5-bromoacetyl-3-thiophenecarboxylate A solution of bromoacetyl bromide (13.52 g, 0.067 mol) in 20 ml of CH$_2$Cl$_2$ was added dropwise to a solution of aluminum chloride (13.4 g, 0.105 mol) in 50 ml of CH$_2$Cl$_2$ at 0° C. The mixture was stirred for 1 h at 0° C., and then a solution of methyl 3-thiophenecarboxylate (9.49 g, 0.067 mol) in CH$_2$Cl$_2$ (50 ml) was added dropwise. The stirring was continued for 12 h and then the mixture was poured over water and ice and extracted with CH$_2$Cl$_2$. The organic phase was washed twice with water, dried over magnesium sulfate and concentrated in a rotary evaporator under vacuum.

The desired compound was purified by flash chromatography on a silica column (20% AcOEt, 80% heptane).
Analysis:
White solid. Mass: 5.95 g. Yield: 34%. m.p.=103–104° C.
$^1$H NMR (CDCl$_3$, 250 MHz): 3.91 (3H, s), 4.36 (2Hs), 8.17 (1H Ar), 8.40 (1H Ar).

(b) Preparation of methyl 5-[(3-iodo-5,5,8,8-tetramethyl-5,6,7,8-tetrahydronaphthalen-2-yloxy)-acetyl]-3-thiophenecarboxylate A solution of 3-iodo-5,5,8,8-tetramethyl-5,6,7,8-tetrahydronaphthalen-2-ol (4 g, 12.1 mmol), methyl 5-bromoacetyl-3-thiophenecarboxylate (3.18 g, 12.1 mmol) and potassium carbonate (1.84 g, 13.3 mmol) in methyl ethyl ketone (100 ml), was heated under reflux for 4 h. The reaction medium was filtered and then concentrated in a rotary evaporator. The mixture was extracted with ethyl ether. The organic phase was washed with water, dried over magnesium sulfate and concentrated in a rotary evaporator under vacuum at 40° C.

The desired compound was purified by flash chromatography on a silica column (60% CH$_2$Cl$_2$, 40% heptane).
Analysis:
White solid. Mass: 6.2 g. Yield: 68%. m.p.=97° C.
$^1$H NMR (CDCl$_3$, 250 MHz): 1.21 (6H, s), 1.23 (6H, s), 1.63 (4H, s), 3.89 (3H, s), 5.05 (2H, s), 6.71 (1H Ar, s), 7.66 (1H Ar, s), 8.39 (1H Ar, s), 8.57 (1H Ar, s).

(c) Preparation of methyl 5-[1-(3-iodo-5,5,8,8-tetramethyl-5,6,7,8-tetrahydronaphthalen-2-yloxymethyl)-vinyl]-3-thiophenecarboxylate A 30% solution of sodium methoxide in methanol (1.68 ml) was added over 8 hours to a mixture of methyl 5-[(3-iodo-5,5,8,8-tetramethyl-5,6,7,8-tetrahydro-naphthalen-2-yloxy)-acetyl]-3-thiophenecarboxylate (4.1 g, 8 mmol) and methyltriphenylphosphine bromide (3.8 g, 10.8 mmol) in THF (50 ml).

The mixture was stirred for 12 h at room temperature. The mixture was concentrated in a rotary evaporator under vacuum at 40° C. It was extracted with ethyl ether and washed with water. The organic phase was then dried over magnesium sulfate and concentrated in a rotary evaporator under vacuum at 40° C.

The desired compound was purified by flash chromatography on a silica column (60% CH$_2$Cl$_2$, 40% heptane).
Analysis:
White solid. Mass: 3.51 g. Yield: 86%. m.p.=94° C. $^1$H NMR (CDCl$_3$, 250 MHz): 1.23 (6H, s), 1.25 (6H, s), 1.64 (4H, s), 3.85 (3H, s), 4.86 (2H, s), 5.59 (1H, s), 5.67 (1H, s), 6.77 (1H Ar, s), 7.58 (1H Ar, s), 7.66 (1H Ar, s), 7.96 (1H Ar, s).
$^{13}$C NMR (CDCl$_3$, 250 MHz): 32.28, 32.19, 34.18, 35.03, 35.36, 52.29, 70.54, 84.37, 115.22, 111.17, 124.76, 132.14, 138.08, 134.12, 136.65, 140.81, 142.76, 147.11, 155.03, 163.44.

(d) Synthesis of methyl [5-(3,5,5,8,8-pentamethyl-2, 3,5,6,7,8-hexahydronaphtho[2,3-b]furan-3-yl) thiophene-3-yl]carboxylate A mixture of tributylamine (3.64 ml, 25.16 mmol), palladium diacetate (74 mg, 0.33 mmol), formic acid (0.28 ml, 7.28 mmol) and methyl 5-[1-(3-iodo-5,5,8,8-tetramethyl-5, 6,7,8-tetrahydronaphthalen-2-yloxymethyl)-vinyl]-3-thiophenecarboxylate (3.38 g, 6.62 mmol) in acetonitrile (100 ml), was heated at 60° C. for 4 h. The reaction medium was concentrated in a rotary evaporator under vacuum at 40° C., treated with water and extracted with ethyl ether. After decantation, the organic phase was washed twice with water, dried over magnesium sulfate and concentrated in a rotary evaporator under vacuum at 40° C.

The desired compound was purified by flash chromatography on a silica column (70% CH$_2$Cl$_2$, 30% heptane).
Analysis:
White solid. Mass: 2.12 g. Yield: 83%. m.p.=117° C.
$^1$H NMR (CDCl$_3$, 250 MHz) : 1.20 (3H, s), 1.23 (3H, s) 1.26 (3H, s), 1.27 (3H, s), 1.65 (4H, s), 1.77 (3H, s), 3.84 (3H, s), 4.40 (1H, d, J=8.6 Hz), 4.52 (2H, d, J=8.6 Hz), 6.79 (1H Ar, s), 7.06 (1H Ar, s), 7.30 (1H Ar, d, J=1.2 Hz), 7.93 (1H Ar, d, J=1.2 Hz).

$^{13}$C NMR (CDCl$_3$, 250 MHz): 27.25, 31.95, 32.02, 32.08, 32.26, 34.17, 34.75, 35.11, 35.19, 48.27, 51.78, 85.42, 107.23, 121.42, 124.04, 131.50, 131.80, 133.00, 137.93, 146.13, 152.87, 157.19, 163.29.

Example 8

Synthesis of [5-(3,5,5,8,8-pentamethyl-2,3,5,6,7,8-hexahydronaphtho[2,3-b]furan-3-yl)thiophene-3-yl] carboxylic acid A mixture of methyl [5-(3,5,5,8,8-pentamethyl-2,3,5,6,7,8-hexahydronaphtho[2,3-b]furan-3-yl)-thiophene-3-yl] carboxylate (2.1 g, 5.4 mmol), lithium hydroxide (2g, 48 mmol), methanol (1 ml) and water (1 ml) in 30 ml of THF was heated under reflux for 6 h. After concentrating in a rotary evaporator under vacuum at 40° C., adding water, ethyl ether and acidifying with a concentrated hydrochloric acid solution to pH 1, the organic phase was washed twice with water, dried over magnesium sulfate and concentrated in a rotary evaporator under vacuum at 40° C. The solids obtained were washed with heptane.
Analysis:

White solid. Mass: 1.8 g. Yield: 92%. m.p.=237° C. $^1$H NMR (DMSO and CDCl$_3$, 250 MHz): 1.20 (3H, s), 1.23 (3H, s), 1.26 (3H, s), 1.27 (3H, s), 1.65 (4H, s), 1.76 (3H, s), 4.40 (1H, d, J=8.6 Hz), 4.52 (2H, d, J=8.6 Hz), 6.77 (1H Ar, s), 7.07 (1H Ar, s), 7.29 (1H Ar, s), 7.93 (1H Ar s).

$^{13}$C NMR (DMSO and CDCl$_3$, 250 MHz): 27.17, 31.84, 31.90, 31.98, 32.13, 34.02, 34.59, 34.97, 35.05, 48.10, 85.29, 106.99, 121.34, 124.23, 131.36, 131.78, 134.00, 137.73, 145.85, 152.39, 157.05, 164.59.

Example 9

Synthesis of [5-(3,5,5,8,8-pentamethyl-2,3,5,6,7,8-hexahydronaphtho[2,3-b]furan-3-yl)thiophen-2-yl] carboxylic acid (a) Preparation of 2-bromoacetyl-5-bromothiophene A solution of bromine (2.9 ml, 56.5 mmol) in 30 ml of CH$_2$Cl$_2$ was added dropwise to a solution of 2-acetyl-5-bromothiophene (10 g, 49 mmol), dioxane (55 ml) and ethyl ether (55 ml). The stirring was continued for 1 h and then the reaction medium was poured into a water/ice mixture and extracted with ethyl ether. The organic phase was washed twice with water, dried over magnesium sulfate and concentrated in a rotary evaporator under vacuum.

The desired compound was purified by recrystallization from heptane.
Analysis:

White solid. Mass: 9.63 g. Yield: 70%. m.p.=92° C.
$^1$H NMR (CDCl$_3$, 250 MHz): 4.28 (2H, s), 7.14 (1H Ar, d, J=4 Hz), 7.55 (1H Ar, d, J=4 Hz).
$^{13}$C NMR (CDCl$_3$, 250 MHz): 29.83, 131.74, 133.92, 183.60

(b) Preparation of 5-bromo-2-[(3-iodo-5,5,8,8-tetramethyl-5,6,7,8-tetrahydronaphthalen-2-yloxy)acetyl]thiophene A solution of 3-iodo-5,5,8,8-tetramethyl-5,6,7,8-tetrahydronaphthalen-2-ol (4 g, 12.1 mmol), 2-bromoacetyl-5-bromothiophene (3.44 g, 12.1 mmol) and potassium carbonate (1.8 g, 13.3 mmol) in methyl ethyl ketone (100 ml), was heated under reflux for 3 h. The reaction medium was filtered and then concentrated in a rotary evaporator, and water and ethyl ether were added. After stirring and decantation, the organic phase was washed twice with water, dried over magnesium sulfate and concentrated in a rotary evaporator under vacuum at 40° C.

The desired compound was purified by flash chromatography on a silica column (5% CH$_2$Cl$_2$, 95% heptane).
Analysis:

White solid. Mass: 4.86 g. Yield: 75%. m.p.=90° C.
$^1$H NMR (CDCl$_3$, 250 Mhz): 1.20 (6H, s), 1.22 (6H, s), 1.63 (4H, s), 4.97 (2H, s), 6.69 (1H Ar, s), 7.14 (1H Ar, d, J=4 Hz), 7.65 (1H Ar, s), 7.96 (1H Ar, d, J=4 Hz).
$^{13}$C NMR (CDCl$_3$, 250 MHz): 31.74, 31.61, 33.76, 34.80, 73.09, 83.07, 124.32, 141.20, 147.10, 154.20, 110.70, 131.60, 134.90, 137.90, 187.70.

(c) Preparation of 5-bromo-2-[1-(3-iodo-5,5,8,8-tetramethyl-5,6,7,8-tetrahydronaphthalen-2-yloxymethyl)vinyl]thiophene A solution of 30% sodium methoxide in methanol (1.65 ml, 8.66 mmol) was added over 8 hours to a mixture of 5-bromo-2-[(3-iodo-5,5,8,8-tetramethyl-5,6,7,8-tetrahydronaphthalen-2-yloxy)acetyl]thiophene (4.3 g, 7.9 mmol) and methyltriphenylphosphine bromide (3.8 g, 10.7 mmol) in THF (45 ml). The mixture was stirred for 12 h at room temperature. The mixture was concentrated in a rotary evaporator under vacuum at 40° C. It was extracted with ethyl ether and washed with water. The organic phase was then dried over magnesium sulfate and concentrated in a rotary evaporator under vacuum at 40° C.

The desired compound was purified by flash chromatography on a silica column (20% CH$_2$Cl$_2$, 80% heptane).
Analysis:

White solid. Mass: 3.26 g. Yield: 78%. m.p.=71° C.
$^1$H NMR (CDCl$_3$, 250 MHz): 1.24 (12H, s), 1.64 (4H, s), 4.81 (2H, s), 5.47 (1H, s), 5.56 (1H, s), 6.75 (1H Ar, s), 6.96 (2H Ar, s), 7.65 (1H Ar, s).
$^{13}$C NMR (CDCl$_3$, 250 MHz): 32.10, 32.20, 34.13, 34.96, 35.27, 70.76, 84.21, 111.13, 125.15, 130.74, 138.03, 112.03, 136.60, 140.78, 143.64, 147.05, 154.99.

(d) Preparation of 5-bromo-2-(3,5,5,8,8-pentamethyl-2,3,5,6,7,8-hexahydronaphtho[2,3-b]furan-3-yl)thiophene A mixture of tributylamine (2.66 ml, 18.39 mmol), palladium diacetate (53 mg, 0.24 mmol), formic acid (0.205 ml, 5.32 mmol) and 5-bromo-2-[1-(3-iodo-5,5,8,8-tetramethyl-5,6,7,8-tetrahydronaphthalen-2-yloxymethyl)-vinyl]thiophene (2.57 mg, 4.84 mmol) in acetonitrile (75 ml) was heated at 60° C. for 4 h. The reaction medium was concentrated in a rotary evaporator under vacuum at 40° C. Water and ethyl ether were added. After decantation, the organic phase was washed twice with 20 ml of water, dried over magnesium sulfate and concentrated in a rotary evaporator under vacuum at 40° C.

The desired compound was purified by flash chromatography on a silica column (20% CH$_2$Cl$_2$, 80% heptane).
Analysis:

White solid. Mass: 2 mg. Yield: 44%. m.p.=110° C.
$^1$H NMR (CDCl$_3$, 250 MHz): 1.24 (6H, s), 1.26 (6H, s), 1.66 (4H, s) 1.72 (3H, s), 4.36 (1H, q, J=8.6 Hz), 4.48 (1H, d, J=8.6 Hz), 6.55 (1H Ar, d, J=3.7 Hz), 6.78 (1H Ar, s), 6.86 (1H Ar, d, J=3.8 Hz), 7.07 (1H Ar, s).
$^{13}$C NMR (CDCl$_3$, 250 MHz): 27.1, 31.1, 32.0, 32.1, 32.3, 34.2, 34.7, 35.1, 35.2, 48.5, 85.4, 107.2, 121.5, 124.0, 129.6, 110.5, 131.4, 137.9, 146.1, 153.4, 157.3.

(e) Synthesis of [5-(3,5,5,8,8-pentamethyl-2,3,5,6,7,8-hexahydronaphtho[2,3-b]furan-3-yl)thiophen-2-yl] carboxylic acid Crystals of iodine and magnesium (58.3 mg, 2.39 mmol) in 0.5 ml of THF were heated and then a solution of 5-bromo-2-(3,5,5,8,8-pentamethyl-2,3,5,6,7,8-hexahydronaphtho [2,3-b]furan-3-yl)thiophene (770 mg, 1.9 mmol) in THF (7 ml) was added dropwise. The mixture was then heated under reflux for 4 h and then cooled to room temperature. Carbon dioxide was bubbled therein for 15 min, and stirring was continued for 12 h. The solution was treated with ethyl ether and acidified with a 2 N hydrochloric acid solution to pH 1.

The organic phase was washed twice with water, dried over magnesium sulfate and concentrated in a rotary evaporator under vacuum at 40° C. The solids obtained were recrystallized by a heptane/ethyl ether mixture.
Analysis:

White solid. Mass: 383 mg. Yield: 54%. m.p.=216° C.
$^1$H NMR (CDCl$_{31}$, 250 MHz): 1.22 (6H, s), 1.24 (3H, s), 1.66 (4H, s), 1.79 (3H, s), 4.42 (1H, d, J=8.6 Hz), 4.54 (1H, d, J=8.6 Hz), 6.80 (1H Ar, s), 6.85 (1H Ar, d, J=3.9 Hz), 7.08 (1H Ar, s), 7.72 (1H Ar, d, J=3.9 Hz).
$^{13}$C NMR (CDCl$_3$, 250 MHz): 27.1, 32.0, 32.1, 32.3, 34.8, 34.2, 35.1, 35.2, 48.8, 85.4, 107.4, 121.4, 124.9, 131.2, 135.2, 138.1, 146.3, 157.3, 161.6, 166.9.

Example 10

Synthesis of [5-(3,5,5,8,8-pentamethyl-2,3,5,6,7,8-hexahydronaphtho[2,3-b]furan-3-yl)thiophen-3-yl] methanol 1 M solution of diisobutylaluminum hydride in toluene (4.2 ml, 4.2 mmol) was added at 0° C. dropwise to a solution of methyl 5-(3,5,5,8,8-pentamethyl-2,3,5,6,7,8-hexahydronaphtho[2,3-b]furan-3-yl)thiophene-3-carboxylate (737 mg, 1.92 mmol) in toluene (30 ml). The solution was stirred for 2 h at 0° C., then treated with a solution of double tartrate of sodium and potassium, filtered and added to a mixture of ethyl ether and water. The organic phase was washed with water, dried over magnesium sulfate and concentrated in a rotary evaporator under vacuum at 40° C.

The desired compound was obtained.
Analysis:

White solid. Mass: 720 mg. Yield: quantitative. m.p.=127° C.
$^1$H NMR (CDCl$_3$, 250 MHz): 1.22 (3H, s), 1.24 (3H, s), 1.27 (6H, s), 1.66 (4H, s), 1.75 (3H, s), 4.38 (1H, d, J=8.5 Hz), 4.52 (1H d, J=8.5 Hz), 4.60 (1H, s), 6.78 (1H Ar, s), 6.82 (1H Ar, s), 7.07 (1H Ar, s), 7.10 (1H Ar, s).
$^{13}$C NMR (CDCl$_3$, 250 MHz): 27.58, 31.98, 32.03, 32.11, 32.28, 34.18, 35.16, 35.25, 48.37, 61.01, 85.62, 107.09, 120.73, 121.57, 123.50, 132.06, 137.72, 141.87, 145.86, 152.98, 157.27.

Example 11

Synthesis of [5-(3,5,5,8,8-pentamethyl-2,3,5,6,7,8-hexahydronaphtho[2,3-b]furan-3-yl)thiophen-3-yl] carbaldehyde A mixture of [5-(3,5,5,8,8-pentamethyl-2,3,5,6,7,8-hexahydronaphtho[2,3-b]furan-3-yl)thiophen-3-yl] methanol (1.4 g, 3.93 mmol) and pyridinium dichromate (2.8 g, 7.4 mmol) in CH$_2$Cl$_2$ (100 ml) was stirred for 3 h at R.T., and then filtered on silica and concentrated in a rotary evaporator under vacuum at 40° C. The desired compound was obtained.
Analysis:

White solid. Mass: 1 g. Yield: 72%. m.p.=138° C.
$^1$H NMR (CDCl$_3$, 250 MHz): 1.21 (3H, s), 1.24 (3H, s), 1.27 (3H, s), 1.28 (3H, s), 1.66 (4H, s), 1.79 (3H, s), 4.41 (1H, d, J=8.6 Hz), 4.53 (1H, d, J=8.6 Hz), 6.80 (1H Ar, s), 7.06 (1H Ar, s), 7.31 (1H Ar, s), 7.96 (1H Ar, s), 9.81 (1H Ar, s)
$^{13}$C NMR (CDCl$_3$, 250 MHz): 27.02, 31.96, 32.02, 32.10, 32.27, 34.19, 34.78, 35.10, 35.18, 48.35, 85.30, 107.34, 121.16, 121.38, 131.55, 136.08, 138.07, 142.79, 146.34, 154.66, 157.22, 185.19.

Example 12

Synthesis of ethyl [5-(3,5,5,8,8-pentamethyl-2,3,5,6,7,8-hexahydronaphtho[2,3-b]furan-3-yl) thiophen-3-yl]acrylate 80% sodium hydride in oil (44 mg, 1.47 mmol) was added to a mixture of [5-(3,5,5,8,8-pentamethyl-2,3,5,6,7,8-hexahydronaphtho[2,3-b]furan-3-yl)thiophen-3-yl] carbaldehyde (400 mg, 1.13 mmol) and triethylphosponoacetate (304 mg, 1.35 mmol) in THF (10 ml). The mixture was stirred for 4 h at room temperature, extracted with ethyl ether and washed with water. After drying, the organic phase was concentrated in a rotary evaporator under vacuum at 40° C.

The desired compound was purified by flash chromatography on a silica column.
Analysis:

White solid. Mass: 430 mg. Yield: 90%. m.p.=104° C.
$^1$H NMR (CDCl$_3$, 250 MHz): 1.22 to 1.35 (5H, m), 1.67 (4H, s) 1.76 (3H, s), 4.24 (2H, q, J=7.3 Hz), 4.40 (1H, d, J=8.6 Hz), 4.52 (1H, d, J=8.6 Hz), 6.17 (1H, d, J=16 Hz), 6.80 (1H Ar, s), 7.01 (1H Ar, d, J=1.3 Hz), 7.08 (1H Ar, s), 7.34 (1H Ar, d, J=1.3 Hz), 7.55 (1H, d, J=16 Hz).
$^{13}$C NMR (CDCl$_3$, 250 MHz): 14.32, 27.31, 31.95, 32.03, 32.09, 32.30, 34.19, 34.76, 35.12, 35.21, 48.35, 60.40, 85.43, 107.23, 117.69, 121.47, 121.49, 127.08, 131.70, 137.32, 137.89, 138.36, 146.10, 153.66, 157.24, 167.22.

Example 13

Synthesis of [5-(3,5,5,8,8-pentamethyl-2,3,5,6,7,8-hexahydronaphtho[2,3-b]furan-3-yl)thiophen-3-yl] acrylic acid A mixture of ethyl [5-(3,5,5,8,8-pentamethyl-2,3,5,6,7,8-hexahydronaphtho[2,3-b]furan-3-yl)thiophen-3-yl]acrylate (430 mg, 1 mmol) and lithium hydroxide (430 mg, [lacuna] mmol) in THF (10 ml) was heated under reflux for 12 h. The mixture was acidified to pH 1 with a concentrated hydrochloric acid solution, extracted with ethyl ether and washed with water. After drying, the organic phase was concentrated in a rotary evaporator under vacuum at 40° C.

The desired compound was purified by flash chromatography on a silica column.
Analysis:

White solid. Mass: 330 mg. Yield: 82%. m.p.=242° C.
$^1$H NMR (CDCl$_3$, 250 MHz): 1.22 (3H, s), 1.25 (3H, s) 1.27 (3H, s), 1.29 (3H, s), 1.67 (4H, s), 1.77 (3H, s), 4.41 (1H, d, J=8.8 Hz), 4.53 (1H, d, J=8.8 Hz), 6.17 (1H, d, J=16 Hz), 6.80 (1H Ar, s), 7.03 (1H Ar, s), 7.09 (1H Ar, s), 7.40 (1H Ar, s), 7.66 (1H Ar, d, J=16 Hz).
$^{13}$C NMR (CDCl$_3$, 250 MHz): 27.72, 32.41, 32.48, 32.54, 32.76, 34.65, 35.22, 35.57, 35.65, 48.83, 85.85, 107.72, 117.04, 121.92, 128.67, 132.06, 137.45, 138.41, 141.15, 146.63, 154.44, 157.68, 172.82.

Example 14

Synthesis of methyl [5-(3,5,5,8,8-pentamethyl-2,3,5,6,7,8--hexahydronaphtho[2,3-b]furan-3-yl)thiophen-3-yl]propynoate (a) Preparation of 3-[4-(2,2-dibromovinyl)thiophen-2-yl]-3,5,5,8,8-pentamethyl-2,3,5,6,7,8-hexahydronaphtho[2,3-b]furan Tetrabromomethane (375 mg, 1.13 mmol) was added to a mixture of triphenylphosphine (440 mg, 1.68 mmol) and zinc (74 mg, 1.13 mmol) in dichloromethane (5 ml) at 0° C. The mixture was stirred at room temperature for 1 h, and then a solution of [5-(3,5,5,8,8-pentamethyl-2,3,5,6,7,8-hexahydronaphtho[2,3-b]furan-3-yl)thiophen-3-yl]carbaldehyde (200 mg, 0.56 mmol) in dichloromethane (2 ml) was added at 0° C. The stirring was continued for 30 min, and then the suspension was filtered on silica. The filtrate was concentrated in a rotary evaporator under vacuum. The desired compound was obtained.

Analysis:

White solid. Mass: 286 mg. Yield: quantitative. m.p.= 124° C.

$^1$H NMR (CDCl$_3$, 250 MHz): 1.22 (3H, s), 1.25 (3H, s), 1.26 (3H, s), 1.27 (3H, s), 1.66 (4H, s), 1.75 (3H, s), 4.39 (1H, d, J=8.5 Hz), 4.51 (1H, d, J=8.5 Hz), 6.79 (1H, s), 7.07 (1H, s), 7.10 (1H, s), 7.36 (1H, s), 7.53 (1H, s).

$^{13}$C NMR (CDCl$_3$, 250 MHz): 27.84, 32.38, 32.48, 32.75, 34.58, 35.15, 35.52, 35.62, 48.70, 85.87, 88.52, 107.59, 121.89, 124.62, 124.87, 131.97, 136.06, 138.23, 146.45, 152.22, 157.66.

(b) Synthesis of methyl [5-(3,5,5,8,8-pentamethyl-2,3,5,6,7,8-hexahydronaphtho[2,3-b]furan-3-yl)thiophen-3-yl]propynoate A 2.5 M solution of butyllithium in hexane (0.82 ml, 2.45 mmol) was added to a solution of 3-[4-(2,2-dibromovinyl)thiophen-2-yl]-3,5,5,8,8-pentamethyl-2,3,5,6,7,8-hexahydronaphtho[2,3-b]furan (478 mg, 0.94 mmol) in THF (5 ml) at −78° C. The stirring was continued for 1 h at −78° C. and then methyl chloroformate (80 μl) was added. The mixture was stirred at room temperature for 1 h, treated with a saturated ammonium chloride solution and extracted with ethyl ether. After washing with water, the organic phase was dried over magnesium sulfate and concentrated in a rotary evaporator under vacuum. The desired compound was purified by column chromatography.

Analysis:

Amorphous solid. Mass: 90 mg. Yield: 24%.

$^1$H NMR (CDCl$_3$, 250 MHz): 1.22 (3H, s), 1.24 (3H, s), 1.27 (3H, s), 1.28 (3H, s), 1.66 (4H, s), 1.76 (3H, s), 3.81 (3H, s), 4.38 (1H, d, J=8.5 Hz), 4.49 (1H, d, J=8.5 Hz), 6.80 (1H, s), 6.93 (1H, d, J=1.1 Hz), 7.06 (1H, s), 7.59 (1H, d, J=1.1 Hz).

$^{13}$C NMR (CDCl$_3$, 250 MHz): 27.00, 31.96, 32.02, 32.12, 32.28, 34.19, 34.77, 35.10, 35.19, 48.23, 52.74, 79.98, 82.30, 85.35, 107.31, 118.33, 121.33, 126.51, 131.43, 132.87, 138.03, 146.30, 153.12, 154.48, 157.23.

Example 15

Synthesis of [5-(3,5,5,8.8-pentamethyl-2,3,5,6,7,8-hexahydronaphtho[2,3-b]furan-3-yl)thiophen-3-yl]propynoic acid The procedure of Example 13 was repeated, but employing methyl [5-(3,5,5,8,8-pentamethyl-2,3,5,6,7,8-hexahydronaphtho[2,3-b]furan-3-yl)thiophen-3-yl]propynoate. The desired compound was obtained.

Analysis:

White solid. Yield: 70%.

$^1$H NMR (CDCl$_3$, 250 MHz): 1.22 (3H, s), 1.25 (3H, s), 1.27 (3H, s), 1.28 (3H, s), 1.66 (4H, s), 1.76 (3H, s), 4.39 (1H, d, J=8.5 Hz), 4.50 (1H, d, J=8.5 Hz), 6.80 (1H, s), 6.96 (1H, d, 1.3 Hz), 7.06 (1H, s), 7.66 (1H, d, J=1.3 Hz).

$^{13}$C NMR (CDCl$_3$, 250 MHz): 27.34, 32.31, 32.36, 32.47, 32.63, 34.54, 35.13, 35.45, 35.54, 48.59, 80.09, 85.07, 85.68, 107.70, 118.36, 121.68, 126.87, 131.74, 134.14, 138.46, 146.71, 153.68, 157.53, 158.22.

B. EXAMPLES OF FORMULATIONS (1) Oral Route (a) The following composition was shaped in the form of a 0.8 g tablet:

| | |
|---|---|
| Compound of Example 1 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets were administered to an adult individual per day for 3 to 6 months depending on the seriousness of the affliction. (b) An oral suspension, intended to be packaged in 5 ml ampoules, was formulated:

| | |
|---|---|
| Compound of Example 2 | 0.050 g |
| Glycerin | 0.500 g |
| 70% sorbitol | 0.500 g |
| Sodium saccharinate | 0.010 g |
| Methyl para-hydroxybenzoate | 0.040 g |
| Flavoring qs | |
| Purified water qs | 5 ml |

For the treatment of acne, 1 ampoule was administered to an adult individual per day for 3 months depending on the seriousness of the affliction.

(c) The following formulation, intended to be packaged in gelatin capsules, was formulated:

| | |
|---|---|
| Compound of Example 3 | 0.025 g |
| Maize starch | 0.060 g |
| Lactose qs | 0.300 g |

The gelatin capsules included gelatin titanium oxide and a preservative.

For the treatment of psoriasis, 1 gelatin capsule is administered to an afflicted adult individual per day for 30 days.

(2) Topical Route (a) The following nonionic water-in-oil cream was formulated:

| | |
|---|---|
| Compound of Example 4 | 0.100 g |
| Mixture of emulsive lanolin alcohols, of waxes and of refined oils, marketed by BDF under the trademark "Eucérine anhydre" | 39.900 g |
| Methyl para-hydroxybenzoate | 0.075 g |
| Propyl para-hydroxybenzoate | 0.075 g |
| Sterile demineralized water qs | 100.000 g |

This cream was applied to a psoriatic skin once or twice per day for 30 days.

(b) A gel was formulated from the following composition:

| | |
|---|---|
| Compound of Example 5 | 0.050 g |
| Erythromycin base | 4.000 g |
| Butylated hydroxytoluene | 0.050 g |
| Hydroxypropylcellulose marketed by Hercules under the trademark "KLUCEL HF" | 2.000 g |
| Ethanol (95%) qs | 100.000 g |

This gel was applied to a skin affected by dermatosis and a skin with acne, one to three times per day for 6 to 12 weeks depending on the seriousness of the affliction:

(c) An antiseborrhoeic lotion was formulated by mixing the following ingredients:

| | |
|---|---|
| Compound of Example 10 | 0.030 g |
| Propyleneglycol | 5.000 g |
| Butylated hydroxytoluene | 0.100 g |
| Ethanol (95%) qs | 100.000 g |

This lotion was applied twice per day to a seborrhoeic scalp and a significant improvement was observed within a period of between 2 and 6 weeks.

(d) A cosmetic/sunscreen composition for combating the harmful effects of the sun was formulated by mixing the following ingredients:

| | |
|---|---|
| Compound of Example 11 | 1.000 g |
| Benzylidencamphor | 4.000 g |
| Fatty acid triglycerides | 31.000 g |
| Glycerol monostearate | 6.000 g |
| Stearic acid | 2.000 g |
| Cetyl alcohol | 1.200 g |
| Lanolin | 4.000 g |
| Preservatives | 0.300 g |
| Propyleneglycol | 2.000 g |
| Triethanolamine | 0.500 g |
| Perfume | 0.400 g |
| Demineralized water qs | 100.000 g |

This composition was applied daily and was effective to combat photoinduced aging.

(e) The following nonionic oil-in-water cream was formulated:

| | |
|---|---|
| Compound of Example 8 | 0.500 g |
| Vitamin D$_3$ | 0.020 g |
| Cetyl alcohol | 4.000 g |
| Glycerol monostearate | 2.500 g |
| PEG 50 stearate | 2.500 g |
| Shea butter | 9.200 g |
| Propyleneglycol | 2.000 g |
| Methyl para-hydroxybenzoate | 0.075 g |
| Propyl para-hydroxybenzoate | 0.075 g |
| Sterile demineralized water qs | 100.000 g |

This cream was applied to a psoriatic skin once or twice per day for 30 days.

(f) A topical gel was formulated by mixing the following ingredients:

| | |
|---|---|
| Compound of Example 15 | 0.050 g |
| Ethanol | 43.000 g |
| α-tocopherol | 0.050 g |
| Carboxyvinyl polymer marketed under the trademark "Carbopol 941" by Goodrich | 0.500 g |
| Triethanolamine in aqueous solution at 20% by weight | 3.800 g |
| Water | 9.300 g |
| Propyleneglycol qs | 100.000 g |

This gel was applied for the treatment of acne 1 to 3 times per day for 6 to 12 weeks depending on the seriousness of the affliction.

(g) A lotion for combating hair loss and for hair regrowth was formulated by mixing the following ingredients:

| | |
|---|---|
| Compound of Example 12 | 0.05 g |
| Compound marketed under the trademark "Minoxidil" | 1.00 g |
| Propyleneglycol | 20.00 g |
| Ethanol | 34.92 g |
| Polyethyleneglycol (molecular weight = 400) | 40.00 g |
| Butylated hydroxyanisole | 0.01 g |
| Butylated hydroxytoluene | 0.02 g |
| Water qs | 100.00 g |

This lotion was applied twice per day for 3 months to a scalp having suffered a substantial hair loss.

(h) An anti-acne cream was formulated by mixing the following ingredients:

| | |
|---|---|
| Compound of Example 9 | 0.050 g |
| Retinoic acid | 0.010 g |
| Mixture of stearates of glycerol and polyethyleneglycol (75 moles) marketed under the trademark "Gelot 64" by GATTEFOSSE | 15.000 g |
| | 15.000 g |
| Polyoxyethylenated kernel oil containing 6 moles of ethylene oxide marketed under the trademark "Labrafil M2130 CS" by GATTEFOSSE | 8.000 g |
| Perhydrosqualene | 10.000 g |
| Preservatives | qs |
| Polyethyleneglycol (molecular weight = 400) | 8.000 g |
| Disodium salt of ethylenediaminetetraacetic acid | 0.050 g |
| Purified water qs | 100.000 g |

This cream was applied to a skin affected by dermatosis or a skin with acne, 1 to 3 times per day for 6 to 12 weeks.

(i) An oil-in-water cream was formulated from the following composition:

| | |
|---|---|
| Compound of Example 6 | 0.020 g |
| Betamethasone 17-valerate | 0.050 g |
| S-carboxymethylcysteine | 3.000 g |
| Polyoxyethylene stearate (40 moles of ethylene oxide marketed under the trademark "Myrj 52" by ATLAS | 4.000 g |
| Sorbitan monolaurate, poloxyethylene containing 20 moles of ethylene oxide marketed under the trademark "Tween 20" by ATLAS | 1.800 g |
| Mixture of glycerol mono- and distearate marketed under the trademark "Géléol" by GATTEFOSSE | 4.200 g |
| Propyleneglycol | 10.000 g |
| Butylated hydroxyanisole | 0.010 g |
| Butylated hydroxytoluene | 0.020 g |
| Ketostearyl alcohol | 6.200 g |
| Preservatives | qs |
| Perhydrosqualene | 18.000 g |
| Mixture of caprylic-capric triglycerides marketed under the trademark "Miglyol 812" by DYNAMIT NOBEL | 4.000 g |
| Triethanolamine (99% by weight) | 2.500 g |
| Water qs | 100.000 g |

This cream was applied twice per day to a skin affected by dermatosis for 30 days.

(j) The following oil-in-water type cream was formulated:

| | |
|---|---|
| Lactic acid | 5.000 g |
| Compound of Example 1 | 0.020 g |
| Polyoxyethylene stearate (40 moles of ethylene oxide) marketed under the trademark "Myrj 52" by ATLAS | 4.000 g |
| Sorbitan monolaurate, polyoxyethylene containing 20 moles of ethylene oxide marketed under the trademark "Tween 20" by ATLAS | 1.800 g |
| Mixture of glycerol mono- and distearate marketed under the trademark "Geleol" by GATTEFOSSE | 4.200 |
| Propyleneglycol | 10.000 g |
| Butylated hydroxyanisole | 0.010 g |
| Butylated hydroxytoluene | 0.020 g |
| Ketostearyl alcohol | 6.200 g |
| Preservatives | qs |
| Perhydrosqualene | 18.000 g |
| Mixture of caprylic-capric triglycerides marketed under the trademark "Miglyol 812" by DYNAMIT NOBEL | 4.000 g |
| Water qs | 100.000 g |

This cream was applied once per day; it combated aging, whether photoinduced or chronologic.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A heterocyclic biaryl compound having the structural formula (I):

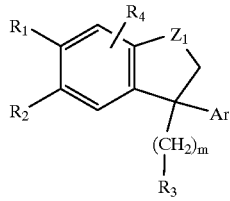

(I)

in which $Z_1$ is O, S or N—r'; $R_1$ and $R_2$, taken together, form with the adjacent aromatic ring a 5- or 6- membered ring optionally substituted with one or more methyl groups and/or optionally interrupted by an SO radical, an $SO_2$ radical, or an oxygen or sulfur atom; $R_3$ is (i) a hydrogen atom, a lower alkyl radical, a lower alkenyl radical, a lower alkynyl radical, a halogen atom, a cyano radical or an —O—$R_7$ radical, wherein $R_7$ is as defined below, (ii) a radical

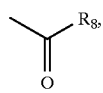

wherein $R_8$ is as defined below, (iii) a radical,

wherein r and r' are as defined below; $R_4$ is (i) a hydrogen atom, (ii) a lower alkyl radical, (iii) a halogen atom, (iv) an —O$R_7$ radical, wherein $R_7$ is as defined below, or (v) a lower acyl radical; Ar is a radical selected from among those of the following formulae (a)–(h):

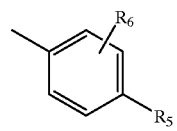

(a)

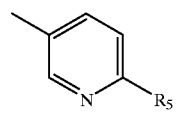

(b)

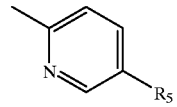

(c)

(d)

(e)

(f)

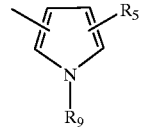

(g)

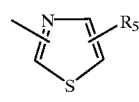

(h)

in which $R_5$ is (i) the radical —$CH_3$, (ii) the radical —$(CH_2)_p$—O—$R_7$, (iii) a radical

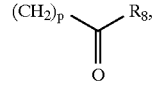

(iv) a radical

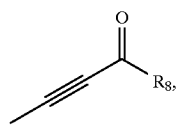

or (v) a radical

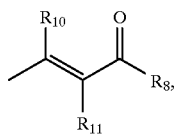

wherein $R_7$, $R_8$, $R_9$, $R_{10}$, $R_{11}$ and p are as defined below; $R_6$ is a hydrogen atom, a halogen atom, a lower alkyl radical, a lower acyl radical or the radical —$OR_7$, wherein $R_7$ is as defined below; the radicals $R_7$, which may be identical or different, are each a hydrogen atom, a lower alkyl radical, an aryl radical, an aralkyl radical, a polyhydroxyalkyl radical, a polyether radical, or a lower acyl radical; the radicals $R_8$, which may be identical or different, are each (a) a hydrogen atom, or a lower alkyl radical, (b) a radical

wherein r and r' are as defined below, or (c) a radical —$OR_{12}$, wherein $R_{12}$ is as defined below; $R_9$ is a hydrogen atom, a lower alkyl radical or a lower acyl radical; the radicals $R_{10}$ and $R_{11}$, which may be identical or different, are each a hydrogen atom or a lower alkyl radical; $R_{12}$ is a hydrogen atom, a lower alkyl radical, a mono- or polyhydroxyalkyl radical, an aryl or aralkyl radical which is (are) optionally substituted, or a sugar or amino acid residue; the radicals r and r', which may be identical or different, are each a protective group comprising an amine function, a hydrogen atom, a lower alkyl radical, an amino acid or sugar residue or, taken together, a heterocycle; m is 0 or 1; and the radicals p, which may be identical or different, are each the numbers 0, 1, 2 or 3; or a pharmaceutically/cosmetically acceptable salt, racemate, optical isomer, or mixture thereof.

2. A heterocyclic biaryl compound as defined by claim 1, wherein in formula (I), Ar has the structure (a).

3. A heterocyclic biaryl compound as defined by claim 1, wherein in formula (I), Ar has the structure (b).

4. A heterocyclic biaryl compound as defined by claim 1, wherein in formula (I), Ar has the structure (c).

5. A heterocyclic biaryl compound as defined by claim 1, wherein in formula (I), Ar has the structure (d).

6. A heterocyclic biaryl compound as defined by claim 1, wherein in formula (I), Ar has the structure (e).

7. A heterocyclic biaryl compound as defined by claim 1, wherein in formula (I), Ar has the structure (f).

8. A heterocyclic biaryl compound as defined by claim 1, wherein in formula (I), Ar has the structure (g).

9. A heterocyclic biaryl compound as defined by claim 1, wherein in formula (I), Ar has the structure (h).

10. A heterocyclic biaryl compound as defined by claim 1, comprising an optical isomer thereof.

11. A heterocyclic biaryl compound as defined by claim 1, comprising a pharmaceutically acceptable salt thereof.

12. A heterocyclic biaryl compound as defined by claim 1, wherein in formula (I), at least one of the following conditions is satisfied:

$R_3$ is a hydrogen atom, $R_4$ is a hydrogen atom, $R_5$ is a radical of formula (iii), (iv) or (v), $R_6$ is a hydrogen atom, $R_8$ is an $OR_{12}$ radical, $R_{12}$ is a hydrogen atom or a lower alkyl radical, Ar is a radical of formula (a), $Z_1$ is an oxygen atom, m=1, p=0.

13. A heterocyclic biaryl compound as defined by claim 1, wherein in formula (I), the lower alkyl radical substituents are selected from among methyl, ethyl, isopropyl, butyl, tert-butyl and hexyl radicals.

14. A heterocyclic biaryl compound as defined by claim 1, wherein in formula (I), the lower acyl radicals have from 1 to 6 carbon atoms.

15. A heterocyclic biaryl compound as defined by claim 1, wherein in formula (I), the cycloaliphatic radicals are selected from among 1-methylcyclohexyl and 1-adamantyl radicals.

16. A heterocyclic biaryl compound as defined by claim 1, wherein in formula (I), the polyhydroxyalkyl radical substituents are selected from among 2,3-dihydroxypropyl, 2,3,4-trihydroxybutyl, 2,3,4,5-tetrahydroxypentyl and pentaerythritol radicals.

17. A heterocyclic biaryl compound as defined by claim 1, wherein in formula (I), the aryl radical substituents are selected from among phenyl radicals optionally substituted by at least one halogen atom, or at least one hydroxyl or nitro functional group, methoxy radical, or optionally substituted amine function.

18. A heterocyclic biaryl compound as defined by claim 1, wherein in formula (I), the aralkyl radical substituents are selected from among benzyl and phenethyl radicals optionally substituted by at least one halogen atom, or at least one hydroxyl or nitro functional group, or methoxy radical.

19. A heterocyclic biaryl compound as defined by claim 1, wherein in formula (I), the alkenyl radical substituents have from 1 to 6 carbon atoms and comprise at least one site of ethylenic unsaturation.

20. A heterocyclic biaryl compound as defined by claim 1, wherein in formula (I), the sugar residue substituents are selected from among those of glucose, galactose, mannose or glucuronic acid.

21. A heterocyclic biaryl compound as defined by claim 1, wherein in formula (I), the amino acid residue substituents are selected from among those comprising a mammalian protein.

22. A heterocyclic biaryl compound as defined by claim 1, wherein in formula (I), the heterocyclic radical substituents are selected from among piperidino, morpholino, pyrrolidino and piperazino radicals which are optionally substituted by a $C_1$–$C_6$ alkyl radical or a mono- or polyhydroxyalkyl radical.

23. A heterocyclic biaryl compound as defined by claim 1, wherein in formula (I), the halogen atom substituents are selected from among fluorine, chlorine and bromine atoms.

24. A heterocyclic biaryl compound as defined by claim 1, selected from among 4-(3,5,5,8,8-pentamethyl-2,3,5,6,7,8-hexahydronaphtho[2,3-b]furan-3-yl)benzoic acid; (+)-4-(3,5,5,8,8-pentamethyl-2,3,5,6,7,8-hexahydronaphtho[2,3-b]furan-3-yl)benzoic acid; 4-(3,5,5,8,8-pentamethyl-2,3,5,6,7,8-hexahydronaphtho[2,3-b]thiophen-3-yl)benzoic acid; (−)-4-(3,5,5,8,8-pentamethyl-2,3,5,6,7,8-hexahydronaphtho[2,3-b]furan-3-yl)benzoic acid; ethyl 4-(3,5,5,8,8-pentamethyl-2,3,5,6,7,8-hexahydronaphtho[2,3-b]furan-3-yl)benzoate; ethyl (+)-4-(3,5,5,8,8-pentamethyl-2,3,5,6,7,8hexahydronaphtho[2,3-b]furan-3-yl)benzoate; ethyl (−)-4-(3,5,5,8,8-pentamethyl-2,3,5,6,7,8-hexahydronaphtho[2,3-b]furan-3-yl)benzoate; methyl [5-(3,5,5,8,8-pentamethyl-2,3,5,6,7,8-hexahydronaphtho[2,3-b]furan-3-yl)thiophen-3-yl]carboxylate; [5-(3,5,5,8,8-pentamethyl-2,3,5,6,7,8- hexahydronaphtho[2,3-b]furan-3-yl)thiophen-3-yl] carboxylic acid; [5-(3,5,5,8,8-pentamethyl-2,3,5,6,7,8-hexahydronaphtho[2,3-b]furan-3-yl)thiophen-2-yl] carboxylic acid; [5-(3,5,5,8,8-pentamethyl-2,3,5,6,7,8-hexahydronaphtho[2,3-b]furan-3-yl)thiophen-3-yl] methanol; [5-(3,5,5,8,8-pentamethyl-2,3,5,6,7,8-hexahydronaphtho[2,3-b]furan-3-yl)thiophen-3-yl] carbaldehyde; ethyl [5-(3,5,5,8,8-pentamethyl-2,3,5,6,7,8-hexahydronaphtho[2,3-b]furan-3-yl)thiophen-3-yl]acrylate; [5-(3,5,5,8,8-pentamethyl-2,3,5,6,7,8-hexahydronaphtho[2,3-b]furan-3-yl)thiophen-3-yl]acrylic acid; methyl [5-(3,5,5,8,8-pentamethyl-2,3,5,6,7,8-hexahydronaphtho[2,3-b]furan-3-yl)thiophen-3-yl]propynoate; and [5-(3,5,5,8,8-pentamethyl-2,3,5,6,7,8-hexahydronaphtho[2,3-b]furan-3-yl)thiophen-3-yl]propynoic acid.

25. A pharmaceutical composition of matter, comprising a therapeutically effective amount of a heterocyclic biaryl compound as defined by claim 1, or pharmaceutically acceptable salt or isomer or racemate thereof, and a pharmaceutically acceptable carrier, vehicle or diluent therefor.

26. The pharmaceutical composition as defined by claim 25, further comprising a retinoid compound, a D vitamin or derivative thereof, a corticosteroid, an anti-free radical agent, an α-hydroxy or α-keto acid or derivative thereof, an ion channel blocker, or combination thereof.

27. The pharmaceutical composition as defined by claim 25, comprising a tablet, a capsule, a syrup, a dragee, a suspension, an elixir, a solution, a powder, granules, an emulsion, microspheres, nanospheres, lipid vesicles, polymeric vesicles, or an injectable.

28. The pharmaceutical composition as defined by claim 25, comprising an ointment, a cream, a milk, an impregnated pad, a gel, a spray, or a lotion.

29. The pharmaceutical composition as defined by claim 25, adopted for topical administration.

30. The pharmaceutical composition as defined by claim 25, adopted for systemic administration.

31. The pharmaceutical composition as defined by claim 25, comprising from 0.001% to 5% by weight of said heterocyclic biaryl compound, or salt or isomer or racemate thereof.

32. A method of treating a keratinization disorder in a mammalian organism in need of such treatment, comprising administering to such organism a therapeutically effective amount of the pharmaceutical composition as defined by claim 25.

33. A method of treating a dermatological disorder in a mammalian organism in need of such treatment, comprising administering to such organism a therapeutically effective amount of the pharmaceutical composition as defined by claim 25.

34. A method of treating a ophthalmological disorder in a mammalian organism in need of such treatment, comprising administering to such organism a therapeutically effective amount of the pharmaceutical composition as defined by claim 25.

35. A method of treating skin aging in a mammalian organism in need of such treatment, comprising administering to such organism a therapeutically effective amount of the pharmaceutical composition as defined by claim 25.

36. A method of treating epidermal and/or dermal atrophy in a mammalian organism in need of such treatment, comprising administering to such organism a therapeutically effective amount of the pharmaceutical composition as defined by claim 25.

37. A method of treating a cicatrization disorder in a mammalian organism in need of such treatment, comprising administering to such organism a therapeutically effective amount of the pharmaceutical composition as defined by claim 25.

38. A method of treating a sebaceous function disorder in a mammalian organism in need of such treatment, comprising administering to such organism a therapeutically effective amount of the pharmaceutical composition as defined by claim 25.

39. A method of treating a cancerous or precancerous disease state in a mammalian organism in need of such treatment, comprising administering to such organism a therapeutically effective amount of the pharmaceutical composition as defined by claim 25.

40. A method of treating inflammation in a mammalian organism in need of such treatment, comprising administering to such organism a therapeutically effective amount of the pharmaceutical composition as defined by claim 25.

41. A method of treating a viral infection in a mammalian organism in need of such treatment, comprising administering to such organism a therapeutically effective amount of the pharmaceutical composition as defined by claim 25.

42. A method of treating or preventing alopecia in a mammalian organism in need of such treatment, comprising administering to such organism a therapeutically effective amount of the pharmaceutical composition as defined by claim 25.

43. A method of treating a cardiovascular disorder in a mammalian organism in need of such treatment, comprising administering to such organism a therapeutically effective amount of the pharmaceutical composition as defined by claim 25.

44. A method of treating a dermatological, rheumatic, respiratory, cardiovascular or ophthalmogic disorder in a mammalian organism in need of such treatment, comprising administering to such organism a therapeutically effective amount of the pharmaceutical composition as defined by claim 25.

45. The method as defined by claim 44, comprising administering to such organism a daily dose of said heterocyclic biaryl compound of about 0.01 mg/kg to 100 mg/kg of body weight thereof.

46. A cosmetic composition of matter, comprising a cosmetically effective amount of a heterocyclic biaryl compound as defined by claim 1, or cosmetically acceptable salt or isomer or racemate thereof, and a cosmetically acceptable carrier, vehicle or diluent therefor.

47. The cosmetic composition as defined by claim 46, comprising a cream, a milk, a lotion, a gel, microspheres, nanospheres, lipid vesicles, polymeric vesicles, a soap, or a shampoo.

48. The cosmetic composition as defined by claim 46, comprising from 0.001% to 3% by weight of said heterocyclic biaryl compound, or salt or isomer or racemate thereof.

49. The cosmetic composition as defined by claim 46, further comprising a retinoid compound, a D vitamin or derivative thereof, a corticosteroid, an anti-free radical agent, an α-hydroxy or α-keto acid or derivative thereof, an ion channel blocker, or combination thereof.

50. A method for treating a skin or hair disorder on a mammalian organism in need of such treatment, comprising administering to such organism a cosmetically/therapeutically effective amount of the cosmetic composition as defined by claim 46.

51. The pharmaceutical composition as defined by claim 25, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

52. The pharmaceutical composition as defined by claim 25, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

53. The cosmetic composition by claim 46, further comprising a wetting agent, a depigmenting agent, a moisturizing agent, an antiseborrhoeic or antiacne agent, an antibiotic, an antifungal agent, a hair regrowth promoter, a nonsteroidal antiinflammatory agent, a carotenoid, an antipsoriatic agent, 5,8,11,14-eicosatetraynoic or 5,8,11-eicosatrynoic acid or ester or amide thereof, or combination thereof.

54. The cosmetic composition as defined by claim 46, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

55. A heterocyclic biaryl compound having the structural formula (I):

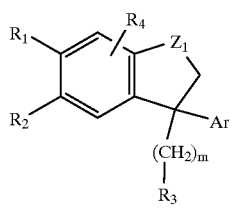

(I)

in which $Z_1$ is O, S or N—r'; $R_1$ and $R_2$, taken together, form with the adjacent aromatic ring a 5- or 6- membered ring optionally substituted with one or more methyl groups and/or optionally interrupted by an SO radical, an $SO_2$ radical, or an oxygen or sulfur atom; $R_3$ is (i) a hydrogen atom, a lower alkyl radical, a lower alkenyl radical, a lower alkenyl radical, a halogen atom, a cyano radical or an —O—$R_7$ radical, wherein $R_7$ is as defined below, (ii) a radical

wherein $R_8$ is as defined below, (iii) a radical,

wherein r and r' are as defined below; $R_4$ is (i) a hydrogen atom, (ii) a lower alkyl radical, (iii) a halogen atom, (iv) an —$OR_7$ radical, wherein $R_7$ is as defined

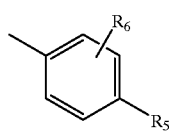

(a)

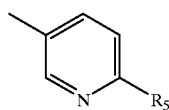

(b)

-continued

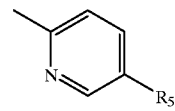

(c)

(d)

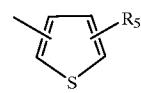

(e)

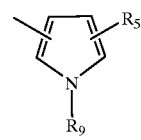

(f)

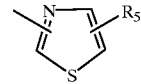

(g)

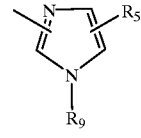

(h)

below, or (v) a lower acyl radical; Ar is a radical selected from among those of the following formulae (a)–(h): in which $R_5$ is (i) the radical —$CH_3$, (ii) the radical —$(CH_2)_p$—O—$R_7$, (iii) a radical

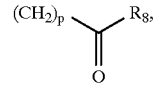

(iv) a radical

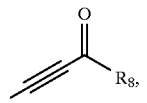

or (v) a radical

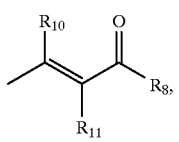

wherein $R_7$, $R_8$, $R_9$, $R_{10}$, $R_{11}$, and p are as defined below; $R_6$ is a hydrogen atom, a halogen atom, a lower alkyl radical, a lower acyl radical or the radical —$OR_7$, wherein $R_7$ is as defined below; the radicals $R_7$, which may be identical or different, are each a hydrogen atom, a lower alkyl radical, an aryl radical, an aralkyl radical, a polyhydroxyalkyl radical; a polyether radical, or a lower acyl radical; the radicals $R_8$, which may be identical or different, are each (a) a hydrogen atom, or a lower alkyl radical, (b) a radical

wherein r and r' are as defined below, or (c) a radical —OR$_{12}$, wherein R$_{12}$ is as defined below; R$_9$ is a hydrogen atom, a lower alkyl radical or a lower acyl radical; the radicals R$_{10}$ and R$_{11}$, which may be identical or different, are each a hydrogen atom or a lower alkyl radical; R$_{12}$ is a hydrogen atom, a lower alkyl radical, a mono- or polyhydroxyalkyl radical, an aryl or aralkyl radical which is (are) optionally substituted, or a sugar or amino acid residue; the radicals r and r', which may be identical or different, are each a protective group comprising an amine function, a hydrogen atom, a lower alkyl radical, an amino acid or sugar residue or, taken together, a heterocycle; m is 1; and the radicals p, which may be identical or different, are each the numbers 0, 1, 2 or 3; or a pharmaceutically/-cosmetically acceptable salt, racemate, optical isomer, or mixture thereof.

* * * * *